US007423138B2

(12) United States Patent
Howley et al.

(10) Patent No.: US 7,423,138 B2
(45) Date of Patent: Sep. 9, 2008

(54) COMPOSITIONS AND METHODS FOR TREATING PAPILLOMAVIRUS-INFECTED CELLS

(75) Inventors: Peter M. Howley, Wellesley, MA (US); Jennifer J. Dowhanick-Morrissette, Pottstown, PA (US); John D. Benson, Brookline, MA (US); Hiroyuki Sakai, Kyoto (JP)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/187,536

(22) Filed: Jul. 1, 2002

(65) Prior Publication Data

US 2003/0092660 A1     May 15, 2003

Related U.S. Application Data

(60) Division of application No. 09/362,012, filed on Jul. 27, 1999, now Pat. No. 6,432,926, which is a continuation-in-part of application No. 08/677,206, filed on Jul. 9, 1996, now abandoned.

(51) Int. Cl.
    *A61K 39/12* (2006.01)
(52) U.S. Cl. .................. 536/23.72; 424/204.1
(58) Field of Classification Search .............. 530/300, 530/350; 536/23.1; 514/12, 44; 435/325, 435/455; 424/204.1
See application file for complete search history.

(56) References Cited

U.S. PATENT DOCUMENTS

| 5,219,990 | A | | 6/1993 | Androphy et al. ........... 530/350 |
|---|---|---|---|---|
| 5,576,206 | A | * | 11/1996 | Schlegel ..................... 435/371 |
| 5,656,599 | A | | 8/1997 | Androphy et al. ............. 514/12 |
| 5,667,965 | A | | 9/1997 | Androphy et al. .............. 435/5 |
| 5,744,133 | A | * | 4/1998 | Lathe et al. ................ 424/93.2 |
| 5,888,516 | A | | 3/1999 | Jansen et al. ............. 424/204.1 |

FOREIGN PATENT DOCUMENTS

| EP | 0 302 758 | 2/1989 |
|---|---|---|
| WO | 0 302 758 | 2/1989 |
| WO | WO 91/15580 | 10/1991 |
| WO | WO 92/12728 | 8/1992 |

OTHER PUBLICATIONS

Goodwin et al., Repression of human papillomavirus oncogenes, PNAS, 2000, 97(23):12513-12518.*
Androphy, E. et al., "Bovine Papillomavirus E2 Trans-activating Gene Product Binds to Specific Sites in Papillomavirus DNA," *Nature*, 325:70-73 (1987).
Barsoum, J. et al., "Mechanism of Action of the Papillomavirus E2 Repressor: Repression in the Absence of DNA Binding," *J. Virol.*, 66:3941-3945 (1992);

Bouvard et al. (1994) "Characterization of the human papillomavirus E2 protein: evidence of trans-activation and trans-repression in cervical keratinocytes" *The Embo Journal*, 13(22):5451-5459.
Choe, J. et al., "Bovine Papillomavirus Type 1 Encodes Two Forms of a Transcriptional Repressor: Structural and Functional Analysis of New Viral cDNAs," *J. Virol.*, 63:1743-1755 (1989).
Dartmann, K. et al., "Short Communications," *Virology*, 151:124-30 (1986).
Dostani, N. et al., "The Functional BPV-1 E2 Trans-activating Protein can Act as a Repressor by Preventing Formation of the Initiation Complex," *Genes & Dev.*, 5:1657-1671 (1991).
Dulic, V. et al., "Altered Regulation of $G_1$ Cyclins in Senescent Human Diploid Fibroblasts: Accumulation of Inactive Cyclin E-Cdk2 and Cyclin D1-Cdk2 Complexes," *Proc. Natl. Acad. Sci. USA*, 90:11034-11038 (1993).
Giri, I. and Yaniv, M., "Structural and Mutational Analysis of E2 Trans-activating Proteins of Papillomaviruses Reveals Three Distinct Functional Domains," *EMBO J.*, 7:2823-29 (1988).
Gloss, B. and Bernard, H., "The E6/E7 Promoter of Human Papillomavirus Type 16 is Activated in the Absence of E2 Proteins by a Sequence-Aberrant Sp1 Distal Element," *J. Virology*, 64:5577-5584 (1990).
Hawley-Nelson, P. et al., "The Specific DNA Recognition Sequence of the Bovine Papillomavirus E2 Protein is and E2-dependent Enhancer," *EMBO J.*, 7:525-31 (1988).
Hirochika, H. et al., "Enhancers and Trans-Acting E2 Transcriptional Factors of Papillomaviruses," *J. Virol.*, 61:2599-606 (1987).
Hwang, E. et al., "Inhibition of Cervical Carcinoma Cell Line Proliferation by the Introduction of a Bovine Papillomavirus Regulatory Gene," *J. Virol.*, 67:3720-3729 (1993).
Lambert, P. et al., "A Transcriptional Repressor Encoded by BPV-1 Shares a Common Carboxy-Terminal Domain with the E2 Transactivator," *Cell*, 50:69-78 (1987).
Li, R., et al., "Specific Recognition Nucleotides and Their DNA Context Determine the Affinity of E2 Protein for 17 Binding Sites in the BPV-1 Genome," *Genes & Dev.*, 3:510-526 (1989).
Matsushime, H. et al., "D-Type Cyclin-Dependent Kinase Activity in Mammalian Cells," *Mol. Cell Biol.*, 14:2066-2076 (1994).

(Continued)

*Primary Examiner*—Stacy B. Chen
(74) *Attorney, Agent, or Firm*—Lahive & Cockfield, LLP; Megan E. Williams; Jill Gorny Sloper

(57) ABSTRACT

By virtue of the present invention, there is provided methods and compositions for interfering with the proliferation of cells infected and/or transformed by papillomaviruses. The processes and compositions of this invention may be used to treat any mammal, including humans. According to this invention, mammals are treated by the pharmaceutically acceptable administration of an $E2_{ad/db}$ protein, either directly or by gene transfer techniques, to reduce the symptoms of the specific papillomavirus-associated disease, or to prevent their recurrence.

10 Claims, 5 Drawing Sheets

OTHER PUBLICATIONS

McBride, A. et al., "Phosphorylation Sites of the E2 Transcriptional Regulatory Proteins of Bovine Papillomavirus Type 1," *J. Virol.*, 63:5076-5085 (1989).

McBride, A. et al., "The Papillomavirus E2 Regulatory Proteins," *J. Biol Chem.*, 266:18411-18414 (1991).

Mohr, I. et al., "Targeting the E1 Replication Protein to the Papillomavirus Origin of Replication by Complex Formation with the E2 Transactivator," *Science*, 250:1654-99 (1990).

Romanczuk, H. et al., "Mutational Analysis of cis Elements Involved in E2 Modulation of Human Papillomavirus Type 16 $P_{97}$ and Type 18 $P_{105}$ Promoters," *J. Virol.*, 64:2849-2859 (1990).

Sousa, R. et al., "Control of Papillomavirus Gene Expression," *Biochemica et Biophysica Acta*, 1032:19-37 (1990).

Spalholz, B. et al., "Characterization of the cis Elements Involved in Basal and E2-Transactivated Expression of the Bovine Papillomavirus $P_{2443}$ Promoter," *J. Virol.*, 65:743-753 (1991).

Stenlund, A. and Botchan, M., "The E2 Trans-Activator can act as a Repressor by Interfering with a Cellular Transcription Factor," *Genes & Dev.*, 4:123-136 (1990).

Thierry, F. and Howley, P., "Functional Analysis of E2-Mediated Repression of the HPV18$P_{105}$ Promoter," *The New Biol.*, 3:90-100 (1991).

Vande Pol, S. and Howley, P., "A Bovine Papillomavirus Constitutive Enhancer is Negatively Regulated by the E2 Repressor Through Competitive Binding for a Cellular Factor," *J. Virol.*, 64:5420-5429 (1990).

Winokur, P. and McBride, A., "Separation of the Transcriptional Activation and Replication Functions of the Bovine Papillomavirus-1 E2 Protein," *EMBO J.*, 11:4111-4118 (1992).

Benson, John. D. et al.., "Amino-Terminal Domains of the Bovine Papillomavirus Type 1 E1 and E2 Proteins Participate in Complex Formation," *J. Virology* 69(7):4364-4372 (1995).

Benson, John D. et al.., "Conserved Interaction of the Papillomavirus E2 Transcriptional Activator Proteins with Human and Yeast TFIIB Proteins," *J. Virology* 71(10):8041-8047 (1997).

Ferguson, Mary K et al.., "Genetic Analysis of the Activation Domain of Bovine Papillomavirus Protein E2: Its Role in Transcription and Replication," *J. Virology* 70(7):4193-4199 (1996).

Goodwin, Edward C. et al.., "Transactivation-Competent Bovine Papillomavirus E2 Protein Is Specifically Required for Efficient Repression of Human Papillomavirus Oncogene Expression and for Acute Growth Inhibition of Cervical Carcinoma Cell Lines," *J. Virology* 72(5):3925-3934 (1998).

Kasukawa, Hiroaki et al.., "A Fifteen-Amino-Acid Peptide Inhibits Human Papillomavirus E1-E2 Interaction and Human Papillomavirus DNA Replication In Vitro," *J. Virology* 72(10):8166-8173 (1998).

Phelps, W. C. et al.., "Molecular targets for human papillomaviruses: prospects for antiviral therapy," *Antiviral Chemistry & Chemotherapy* 9:359-377 (1998).

Sakai, Hiroyuki et al.., "Targeted Mutagenesis of the Human Papillomavirus Type 16 E2 Transactivation Domain Reveals Separable Transcriptional Activation and DNA Replicaiton Functions," *J. Virology* 70(3):1602-1611 (1996).

Yasugi, Toshiharu et al.., "Mapping and Characterization of the Interaction Domains of Human Papillomavirus Type 16 E1 and E2 Proteins," *J. Virology* 71(2):891-899 (1997).

Yasugi, Toshiharu et al.., "Two Classes of Human Papillomavirus Type 16 E1 Mutants Suggest Pleiotropic Conformational Constraints Affecting E1 Multimerization, E2 Interaction, and Interaction with Cellular Proteins," *J. Virology* 71(8):5942-5951 (1997).

Crystal, Ronald G., "Transfer of genes to humans: early lessons and obstacles to success," *Science* 270:404-410 (1995).

Mastrangelo et al.., "Gene therapy for human cancer: an essay for clinicians," Seminars in *Oncology* 23(1): 4-21 (1996).

Androphy, E. et al.., "Bovine Papillomavirus E2 Trans-activating Gene Product Binds to Specific Sites in Papillomavirus DNA," *Nature*, 325:70-73 (1987).

Barsoum, J. et al.., "Mechanism of Action of the Papillomavirus E2 Repressor: Repression in the Absence of DNA Binding," *J. Virol.*, 66:3941-3945 (1992).

Benson, John D. et al.., "Conserved Interaction of the Papillomavirus E2 Transcriptional Activator Proteins with Human and Yeast TFIIB Proteins," *J. Virology* 71(10):8041-8047 (1997).

Benson, John. D. et al.., "Amino-Terminal Domains of the Bovine Papillomavirus Type 1 E1 and E2 Proteins Participate in Complex Formation," *J. Virology* 69(7):4364-4372 (1995).

Bouvard et al.. (1994) "Characterization of the human papillomavirus E2 protein: evidence of trans-activation and trans-repression in cervical keratinocytes" *The Embo Journal*, 13(22):5451-5459.

Choe, J. et al.., "Bovine Papillomavirus Type 1 Encodes Two Forms of a Transcriptional Repressor: Structural and Functional Analysis of New Viral cDNAs," *J. Virol.*, 63:1743-1755 (1989.

Coghlan, *New Scientist*, vol. 148, pp. 14-15 (1995).

Crystal, Ronald G., "Transfer of genes to humans: early lessons and obstacles to success," *Science* 270:404-410 (1995).

Dartmann, K. et al.., "Short Communications," *Virology*, 151:124-30 (1986).

Dostani, N. et al.., "Functional BPV-1 E2 Trans-activating Protein can Act as a Repressor by Preventing Formation of the Initiation Complex," *Genes & Dev.*, 5:1657-1671 (1991).

Dulic, V. et al.., "Altered Regulation of G1 Cyclins in Senescent Human Diploid Fibroblasts: Accumulation of Inactive Cyclin E-Cdk2 and Cyclin D1-Cdk2 Complexes," *Proc. Natl. Acad. Sci. USA*, 90:11034-11038 (1993).

Ferguson, Mary K et al.., "Genetic Analysis of the Activation Domain of Bovine Papillomavirus Protein E2: Its Role in Transcription and Replication," *J. Virology* 70(7):4193-4199 (1996).

Giri, I. and Yaniv, M., "Sturctural and Mutational Analysis of E2 Trans-activating Proteins of Papillomaviruses Reveals Three Distinct Functional Domains," *EMBO J.*, 7:2823-29 (1988).

Gloss, B. and Bernard, H., "The E6/E7 Promoter of Human Papillomavirus Type 16 is Activated in the Absence of E2 Proteins by a Sequence-Aberrant Sp1 Distal Element," *J. Virology*, 64:5577-5584 (1990).

Goodwin, Edward C. et al.., "Transactivation-Competent Bovine Papillomavirus E2 Protein Is Specifically Required for Efficient Repression of Human Papillomavirus Oncogene Expression and for Acute Growth Inhibiton of Cervical Carcinoma Cell Lines," *J. Virology* 72(5):3925-3934 (1998).

Hawley-Nelson, P. et al.., "The Specific DNA Recognition Sequence of the Bovine Papillomavirus E2 Protein is an E2-dependent Enhancer," *EMBO J.*, 7:525-31 (1988).

Hirochika, H. et al.., "Enhancers and Trans-Acting E2 Transcriptional Factors of Papillomaviruses," *J. Virol.*, 61:2599-606 (1987).

Hwang, E. et al.., "Inhibition of Cervical Carcinoma Cell Line Proliferation by the Introduction of a Bovine Papillomavirus Regulatory Gene," *J. Virol.*, 67:3720-3729 (1993).

Kasukawa, Hiroaki et al.., "A Fifteen-Amino-Acid Peptide Inhibits Human Papillomavirus E1-E2 Interaction and Human Papillomavirus DNA Replication In Vitro," *J. Virology* 72(10):8166-8173 (1998).

Lambert, P. et al.., "A Transcriptional Repressor Encoded by BPV-1 Shares a Common Carboxy-Terminal Domain with the 32 Transactivator," *Cell*, 50:69-78 (1987)..

Li, R., et al.., "Specific Recognition Nucleotides and Their DNA Context Determine the Affinity of E2 Protein for 17 Binding Sites in the BPV-1 Genome," *Genes & Dev.*, 3:510-526 (1989).

Mastrangelo et al.., "Gene therapy for human cancer: an essay for clinicians," Seminars in *Oncology* 23(1):4-21 (1996).

Matsushime, H. et al.., "D-Type Cyclin-Dependent Kinase Activity in Mammalian Cells," *Mol. Cell Biol.*, 14:2066-2076 (1994).

McBride, A. et al.., "Phosphorylation Sites of the E2 Transcriptional Regulatory Proteins of Bovine Papillomavirus Type 1," *J. Virol.*, 63:5076-5085 (1989).

McBride, A. et al.., "The Papillomavirus E2 Regulatory Proteins," *J. Biol Chem.*, 266:18411-18414 (1991).

Mohr, I. et al.., "Targeting the E1 Replication Protein to the Papillomavirus Origin of Replication by Complex Formation with the E2 Transactivator," *Science*, 250:1654-99 (1990).

Phelps, W. C. et al.., "Molecular targets for human papillomaviruses: prospects for antiviral therapy," *Antiviral Chemistry & Chemotherapy* 9:359-377 (1998).

Romanczuk, H. et al.., "Mutational Analysis of cis Elements Involved in E2 Modulation of Human Papillomavirus Type 16 P97 and Type 18 P105 Promoters," *J. Virol.*, 64:2849-2859 (1990).

Sakai, Hiroyuki et al.., "Targeted Mutagenesis of Human Papillomavirus Type 16 E2 Transactivation Domain Reveals Separable Transcriptional Activation and DNA Replication Functions," *J. Virology* (70(3):1602-1611 (1996).

Sousa, et al.., "Control of Papillomavirus Gene Expression," *Biochemica et Biophysica Acta*, 1032:19-37 (1990).

Spalholz, B. et al.., "Characterization of the cis Elements Involved in Basal and E2-Transactivated Expression of the Bovine Papillomavirus P2443 Promoter," *J. Virol.*, 65:743-753 (1971).

Stenlund, A. and Bolchan, M., "The E2 Trans-Activator can act as a Repressor by Interfering with a Cellular Transcription Factor," *Genes & Dev.*, 4:123-136 (1990).

Thierry, F. and Howley, P., "Functional Analysis of E2-Mediated Repression of the HPV18P105 Promoter," *The New Biol.*, 3:90-100 (1991).

Vande Pol, S. and Howley, P., "A Bovine Papillomavirus Constitutive Enhancer is Negatively Regulated by the E2 Repressor Through Competitive Binding for a Cellular Factor," *J. Virol.*, 64:5420-5429 (1990).

Winokur, P. and McBride, A., "Separation of the Transcriptional Activation and Replication Functions of the Bovine Papillomavirus-1 E2 Proteins," *EMBO J.*, 11:4111-4118 (1992).

Yasugi, Toshiharu et al.., "Mapping and Characterization of the Interaction Domains of Human Papillomavirus Type 16 E1 and E2 Proteins," *J. Virology* 71(2):891-899 (1997).

Yasugi, Toshiharu et al.., "Two Classes of Human Papillomavirus Type 16 E1 Mutants Suggest Pleiotropic Conformational Constraints Affecting E1 Multimerization, E2 Interaction, and Interaction with Cellular Proteins," *J. Virology* 71(8):5942-5951 (1997).

* cited by examiner

|  | | E2 Properties | | G418 resistant colonies | |
|---|---|---|---|---|---|
|  |  | DNA replication | Transcriptional trans-activation | Exp. 1 | Exp. 2 |
| E2 Δ1-15 | 15 ──── 410 | − | − | 38 | 46 |
| E2 1-218 | 1 ──── 218 | + | − | 82 | 47 |
| E2 Δ157-282 | 1 ──156 283──410 | − | − | 69 | 52 |
| E2 Δ220-309 | 1 ──219 310──410 | − | + | 0 | 0 |
| E2TA | 1 ──── 410 | + | + | 0 | 0 |
| Vector Alone |  | NA | NA | 42 | 55 |

*FIG. 3A*

| | | E2 Properties | | | G418 resistant colonies | |
|---|---|---|---|---|---|---|
| | transcriptional transactivation | dimerization | DNA binding | | Exp. 1 | Exp. 2 |
| spi-E2 | + | + | + | | 78 | 80 |
| VP16-E2 | + | + | + | | 92 | 114 |
| E2-TA | + | + | + | | 0 | 0 |
| E2 (I 331 R) | - | - | - | | 45 | 73 |
| E2 (R 344 K) | - | + | - | | 51 | 58 |

*FIG. 3B*

COMPOSITIONS AND METHODS FOR TREATING PAPILLOMAVIRUS-INFECTED CELLS

RELATED APPLICATIONS

This application is a divisional of U.S. application Ser. No. 09/362,012 filed Jul. 27, 1999, now U.S. Pat. No. 6,432,926, which is a continuation-in-part application of U.S. application Ser. No. 08/677,206 filed on Jul. 9, 1996, now abandoned. The entire contents of the aforementioned applications and all other patents, patent applications, and references cited throughout this specification are hereby incorporated by reference in their entireties.

BACKGROUND OF THE INVENTION

Papillomaviruses (PV) have been linked to widespread, serious human diseases, especially carcinomas of the genital and oral mucosa. Tens of millions of women suffer from human papilloma virus (HPV) infection of the genital tract. Significant number of these women eventually develop cancer of the cervix. It has been estimated that perhaps twenty percent (20%) of all cancer deaths in women worldwide are from cancers which are associated with HPV. As many as 90% of all cervical cancer maybe linked to HPV.

Papillomaviruses also induce benign, dysplastic and malignant hyperproliferations of skin and mucosal epithelium (see, for example, Mansur and Androphy, (1993) *Biochim Biophys Acta* 1155:323-345; Pfister (1984) *Rev. Physiol. Biochem. Pharmacol.* 99:111-181; and Broker et al. (1986) *Cancer Cells* 4:17-36, for reviews of the molecular, cellular, and clinical aspects of the papillomaviruses).

HPV's are a heterogeneous group of DNA tumor viruses associated with hyperplastic (warts, condylomata), pre-malignant and malignant lesions (carcinomas) of squamous epithelium. Almost 70 HPV types have been identified, and different papillomavirus types are known to cause distinct diseases, c.f., zur Hausen, (1991) *Virology* 184:9-13; Pfister, (1987) *Adv. Cancer Res.*, 48:113-147; and Syrjanen, (1984) *Obstet. Gynecol. Survey* 39:252-265. HPVs can be further classified either high risk (such as HPV type 16 [HPV-16] and HPV-18) or low risk (e.g, HPV-6 and HPV-11) on the basis of the clinical lesions with which they are associated and the relative propensity for these lesions to progress to cancer. For example, HPV types 1 and 2 cause common warts, and types 6 and 11 cause warts of the external genitalia, anus and cervix. HPV's can be isolated from the majority of cervical cancers, e.g., approximately 85 to 90% of human cervical cancers harbor the DNA of a high-risk HPV. Types 16, 18, 31 and 33 are particularly common; HPV-16 is present in about 50 percent of all cervical cancers.

The biological life cycle of the papillomaviruses appears to differ from most other viral pathogens. These viruses are believed to infect the basal or germ cells of the epithelium. Rather than proceeding to a lytic infection in which viral replication kills the cell, viral DNA transcription and replication are maintained at very low levels until higher strata of the epithelium are achieved. There, presumably in response to differentiation-specific signals, viral transcription accelerates, DNA synthesis begins and virion assemble occurs.

In HPV-positive genital cancers, the viral genomes are transcriptionally active, and two viral genes, E6 and E7, are invariably expressed. The high-risk HPVs encode two oncoproteins, E6 and E7, whose expression can extend the life span of squamous epithelial cells, which are a normal host cell for the papillomavirus. E6 and E7 together can result in the efficient immortalization of primary human cells (Hawley-Nelson et al., (1989) *EMBO J.*, 8:3905-3910; Münger et al., (1989) *J. Virol.*, 63:4417-4421; Watanabe et al., (1989) *J. Virol.*, 63:965-969). E6 and E7 are expressed in HPV-positive cervical cancer-derived cell lines (Schneider-Gädicke et al., (1986) *EMBO J.*, 5:2285-2292; Schwarz et al., (1985) *Nature*, (London) 314:111-114; Smotkin et al., (1986) *Proc. Natl. Acad. Sci. USA*, 83:4680-4684). Furthermore, although many genetic changes have occurred in cervical carcinoma cells, the continued expression of the viral oncoproteins is necessary since expression of antisense E6/E7 RNA results in decreased cell growth (von Knebel-Doeberitz et al., (1988) *Cancer Res.*, 48:3780-3785). Similar to the transforming proteins of the other small DNA tumor viruses, simian virus (SV40) and adenovirus, the transforming properties of the E6 and E7 oncoproteins appear to be due at least in part to their capacity to functionally inactivate the p53 and the retinoblastoma (pRB) tumor suppressor proteins. The E6 proteins of HPV-16 and HPV-18 can complex and cause ubiquination-dependent degradation of p53 (Wemess et al., (1990) *Science*, 248:76-79; Schiffaer et al., *Cell* 75:495-505 (1993)). The high-risk HPV E7 proteins bind pRB more efficiently than the E7 proteins of low-risk HPVs (Barbosa et al., (1990) *EMBO J.*, 9:153-160; Dyson et al., (1989) *Science*, 243:934-937; Münger et al., (1989) *EMBO J.*, 8:4099-4015). It is believed that the functional inactivation of both p53 and pRB, and related regulatory pathways, by E6 and E7 are important steps in cervical carcinogenesis.

One characteristic of HPV-related carcinogenic progression is the frequent integration of the viral genome into the human chromosome in the cancer cells in a manner that results in the loss of expression of the viral E2 gene but maintains high levels of E6/E7 expression (Dürst et al., (1985) *J. Gen. Virol.*, 66:1515-1522; Jeon et al., (1995) *Proc. Natl. Acad. Sci. USA*, 92:1654-1658). The product of the E2 open reading frame plays an important role in the complex transcriptional pattern of the HPV's. The E2 transcriptional activation protein ("the E2 protein") is a trans-acting factor that activates transcription through specific binding to cis-acting E2 enhancer sequences in viral DNA (Androphy et al., (1987) *Nature*, 324:70-73), and has been shown to induce promoter expression in a classical enhancer mechanism (Spalholz et al., (1985) *Cell* 42:183-91). The E2 gene product exerts trans-regulatory effects in the upstream regulatory region ("LCR") of the viral genome, disruption of E2 is thought to alter regulation of expression of E6 and E7 genes.

As with other transcription factors, the functions of the E2 proteins appear to be localized in discrete domains (Giri et al., (1988) *EMBO J.*, 7:2923-29). The E2 amino terminus encompasses the transcriptional activation domain and binding site for the papillomavirus E1 replication protein. The E2 C-terminal domain is well conserved among the papillomaviruses, and contains the dimerization and DNA binding activities of E2. This domain sponsors sequence-specific interaction with DNA containing the sequence ACC(G)NNNN((C)GGT and represses the papillomavirus early promoter that drives expression of E6 and E7 (e.g., the P97 promoter of HPV16 and the P105 promoter of HPV 18). This is due to the position of E2 binding sites within the promoter: two of the four E2 binding sites within the P97 and P105 promoters immediately flank the TATA box and promoter proximal SP1 sites of these promoters, rendering them inaccessible to needed transcription factors.

The upstream regulatory region (or long control region (LCR)) is found immediately 5' to the early genes of bovine papilloma viruses (BPV's) and other papillomaviruses. The LCR contains cis-acting regulatory signals, including an origin of DNA replication and several promoters that function in early transcription. The LCR also contains enhancer elements that activate transcription from the URR promoters and heterologous promoters (Sousa et al., (1990) *Biochemica et Biophysica Acta* 1032: 19-37).

The E2 enhancer elements are conditional, in that they stimulate transcription only when activated by a protein encoded by the E2 open reading frame (Romanczuk et al., (1990) *J. of Virol.* 64:2849-2859). Gene products from the E2 gene include the full-length transcriptional activator E2 protein and at least two truncated versions of the E2 protein BPV1 that function as transcriptional repressors. Transcriptional activation and repression of viral genes by E2 gene products constitute critical regulatory circuits in papillomavirus gene expression and DNA replication (reviewed in McBride et al., (1991) *J. Biol. Chem.* 266:18411-18414). Within the LCR, transcriptional regulation by the E2 protein depends on its direct binding to the nucleotide sequence 5'ACC(G)NNNN(C)GGT3' (SEQ ID NO:9) (Androphy et al., supra; Dartmann et al., (1986) *Virology*, 151:124-30; Hirochika et al., (1987) *J. Virol*, 61:2599-606; P. Hawley-Nelson et al., (1988) *EMBO J.*, 7:525-31; McBride et al., (1988) *EMBO J.*, 7:533-39; McBride et al., *J. of Biol. Chemistry* 266:18411-1844 (1991); Demeret et al. *J. Virol.* 71:9343-9349 (1997); Desaintes et al. *EMBO* 16:504-514 (1997); Thierry et al. *New Biol.* 10:4431-4437 (1990); and Bernard et al. *J. Virol.* 63:4317-4324 (1989)).

European patent application 302,758 refers to the use of modified forms of E2 protein that bind to, and block, E2 binding sites on papillomavirus DNA without resulting in trans-activation. That application also refers to repression of E2 transcriptional activation through the use of DNA fragments that mimic E2 binding sites, and thus bind with E2 trans-activators, making them unavailable for binding to E2 sites on the viral DNA.

U.S. Pat. No. 5,219,990 describes the use of E2 transactivation repressors which interfere with normal functioning of the native full-length E2 transcriptional activation protein of the papillomavirus. However, the E2 trans-activation repressors of the '990 patent are proteins that dimerize with the full-length native E2 protein to form inactive heterodimers, thus interfering with the formation of active homodimers comprising full-length native E2 polypeptides and thereby repressing papillomavirus transcription and replication. The E2 trans-activation repressors are described as fragments of the E2 polypeptide in which the dimerization function has been separated from its DNA binding function, e.g., the E2 trans-activation repressors includes at least the dimerization region, but less than the DNA binding domain, of the E2 polypeptide.

SUMMARY OF THE INVENTION

One aspect of the present invention provides a method of treating, e.g., lessening the severity or preventing the reoccurrence of, a papillomavirus-induced condition. In general, the subject method comprises administering to an animal, e.g. a human, infected with a papillomavirus a pharmaceutical preparation comprising a therapeutically effective amount of either (i) an $E2_{ad/db}$ polypeptide or (ii) a gene construct for expressing the $E2_{ad/db}$ polypeptide. As described in further detail below, the $E2_{ad/db}$ polypeptide includes a DNA binding domain and a transcriptional activation domain derived from one or more E2 proteins. The E2 polypeptide or gene construct is formulated in the pharmaceutical preparation for delivery into PV-infected cells of the animal.

In preferred embodiments, the subject method is used to treat a human who is infected with a human papillomavirus (HPV), particularly a high risk HPV such as HPV-16, HPV-18, HPV-31 and HPV-33. However, treatment of low risk HPV conditions is also specifically contemplated.

In certain preferred embodiments, the DNA binding and transcriptional activation domains of the $E2_{ad/db}$ polypeptide have amino acid sequences corresponding to an E2 protein(s) from an HPV, including especially, an E2 protein from a high risk HPV. The DNA binding domain and transcriptional activation domain of the E2 polypeptide can be one contiguous polypeptide chain, or in those embodiments where the E2 protein is directly formulated into the therapeutic composition, the DNA binding and transcriptional activation domain portions of the therapeutic E2 polypeptide can be provided as two separate peptide chains which have been chemically cross-linked, e.g., other than by a amide bond. The $E2_{ad/db}$ polypeptide can be a full length E2 protein, e.g., also including a hinge region sequence or the like, or can lack other E2 peptide sequences except for the DNA binding and transcriptional activation domains. The $E2_{ad/db}$ polypeptide may be derived from any species, e.g., human, bovine, rabbit, and from any papillomavirus subtype. In a preferred embodiment the $E2_{ad/db}$ has an alteration, for example, a E39A substitution or an altered hinge region, e.g., a deletion of residues corresponding to BPV $E2_{\Delta 220-309}$.

The subject method can be used to inhibit pathological progression of papillomavirus infection, such as preventing or reversing the formation of warts, e.g. Plantar warts (*verruca plantaris*), common warts (*verruca plana*), Butcher's common warts, flat warts, genital warts (*condyloma acuminatum*), or epidermodysplasia verruciformis; as well as treating papillomavirus-infected cells which have become, or are at risk of becoming, transformed and/or immortalized, e.g. cancerous, e.g. a laryngeal papilloma, a focal epithelial, a cervical carcinoma.

Another aspect of the present invention relates to a pharmaceutical preparation comprising a therapeutically effective amount of a recombinant transfection system for ameliorating a papillomavirus-induced condition in a subject. For instance, the transfection system, which is for gene therapy, includes a gene construct having a nucleic acid encoding an $E2_{ad/db}$ polypeptide and operably linked to a transcriptional regulatory sequence for causing expression of the E2 polypeptide in eukaryotic cells. The gene construct is provided in a gene delivery composition for delivering the gene construct to a papillomavirus infected cells and causing the cell to be transfected with the gene construct. For example, the gene delivery composition can be, e.g., a recombinant viral particle, a liposome, a poly-cationic nucleic acid binding agent, or a gene therapy vector derived from, e.g., a retrovirus, adeno-associated virus, or adenovirus.

Yet another aspect of the invention relates to a pharmaceutical preparation comprising a therapeutically effective amount of an $E2_{ad/db}$ polypeptide, formulated in the pharmaceutical preparation for delivery into PV-infected cells of an animal. In preferred embodiments, the polypeptide is formulated as a liposome.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide*

Synthesis (M. J. Gait ed., 1984); Mullis et al. U.S. Pat. No.: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

BRIEF DESCRIPTION OF THE FIGURES

FIGS. 3A and 3B illustrate the results of mutational analysis of E2 proteins. FIG. 3A shows that the E2 hinge region is not required for growth suppression. FIG. 3B shows that the E2 transactivation domain, and a functional E2 DNA binding domain are both required for growth arrest. The properties of the various E2 proteins are also listed

DETAILED DESCRIPTION OF THE INVENTION

Figure 1:
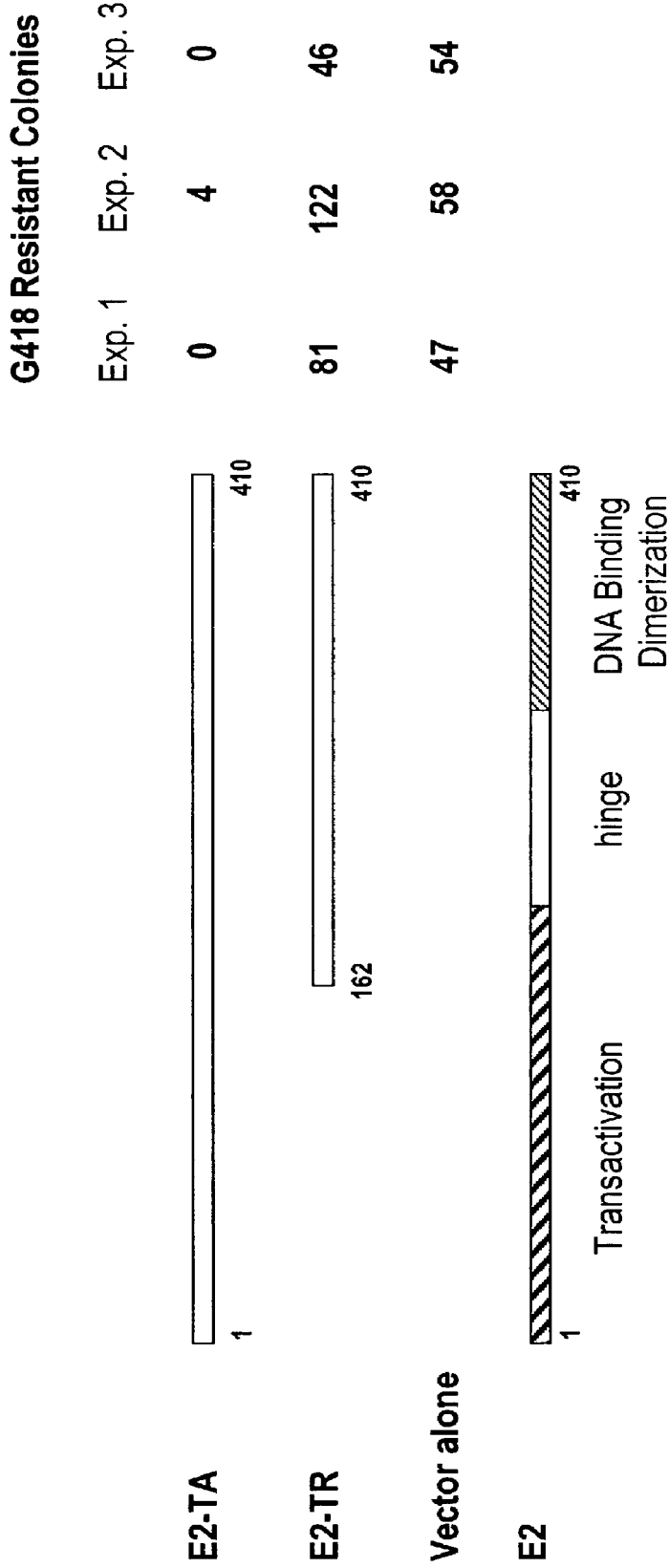
FIG. 1 schematically illustrates the growth suppression by the full length BPV E2 protein, but not E2-TR. The gross domain structure of the papillomavirus E2 proteins is also illustrated.

The papillomaviruses (PV) are infectious agents that can cause benign epithelial tumors, or warts, in their natural hosts. Infection with specific human papillomaviruses (HPV) is also associated with human epithelial malignancies, including malignancies of the uterine cervix, genitalia, skin and, though less frequently, other sites.

The analysis of the temporal expression of mRNAs and the nucleotide sequence of human and animal papillomavirus (PV) genomes has revealed overall structural similarities in their genetic organization. There are at least seven open reading frames (ORFs) in all PVs, and differential RNA splicing provides the capability to produce several additional proteins. The genes that are required for viral replication are typically designated with the prefix "E" (for "early"), being expressed before the "L" or "late" genes. The products of the papillomavirus E2 open reading frame play a key role in the regulation of the viral cycle, affecting both transcription and replication. For instance, the E2 transcriptional activation protein (herein the "E2 protein") is a trans-acting factor that activates transcription through specific binding to cis-acting E2 enhancer sequences. The 410 amino acid papillomavirus E2 protein has been shown to induce promoter expression in a classical enhancer mechanism (Spalholz et al. Cell (1985) 42:183-91). The E2 protein appears to provide both positive and negative feedback loops for viral gene expression.

As with other transcription factors, the functions of the E2 protein appear to be localized to discrete modular domains (Giri et al. (1988) EMBO J. 7:2823-2829). The C-terminal domain of the E2 polypeptide is responsible for recognition of E2 binding sites on viral DNA, and is accordingly referred to herein as the "DNA binding domain". The N-terminal domain of the E2 polypeptide is responsible for transcriptional activation following binding of the protein to viral DNA, and is referred to as the "transactivation domain".

In bovine papillomavirus models, and in some human papillomaviruses, at least two N-terminally truncated E2 proteins occur naturally and act as native repressors. It has been experimentally confirmed in vitro that truncated forms of E2 proteins which retain their ability to bind DNA but do not trans-activate, are competitive inhibitors of trans-activation-competent E2 polypeptides (Lambert et al. (1987) Cell 50:69-78; Stenlund et al. (1990) Genes Dev. 4:123-136; and Choe et al. (1989) J. Virol. 63:1743-1755; McBride et al. (1991) J. Bio. Chem. 266:18411-18414.

As described in the appended examples, we have discovered that HPV E2 proteins which retain both transactivation and DNA binding domains ("$E2_{ad/db}$" proteins, e.g., BPV $E2_{\Delta 220\text{-}309}$ and HPV $E2_{(E39A)}$) are capable of inhibiting cell growth of HPV-infected and/or HPV-transformed cells. On the other hand, contrary to certain teachings in the art, we observed that growth of both HPV-infected and HPV-transformed cells was not apparently inhibited by the E2 transcriptional repressor (E2-TR) which represents the DNA binding domain of the E2 protein nor by VP16-E2. This result was somewhat surprising because previous studies found that N-terminally deleted forms of both the HPV and BPV forms of the E2 protein were able to transcriptionally repress the E6/E7 promoter (Thierry et al., (1991) New Biol., 3:90-100). The data presented below suggests that the mechanism for E2-mediated growth suppression may involve more complex mechanisms or that the E2 DNA binding domain is not, in and of itself, an effective repressor of the HPV promoters integrated into the host chromosome.

Progression of high-risk HPV lesions to cervical cancer is almost invariably associated with integration of the viral genome with disruption of the E1/E2 region (Baker C. C. (1993) In: S. O'Brien (ed.) Genetic maps: locus maps of complex genomes, Cold Spring Harbor Laboratory Press, p. 1.134-1.146). This integration leads to the deregulation of the expression of the viral E6 and E7 transforming genes. This may be due in part to the release of the E6/E7 promoter from the repressor effects of E2. The data set forth below demonstrates that the E2 protein can inhibit growth of HPV-immortalized cells. Moreover, we have shown that HPV-positive cervical carcinoma cells are sensitive to the reintroduction of HPV E2 proteins; their growth is inhibited by expression of $E2_{ad/db}$ proteins. While not being bound by any particular theory, the growth-suppressive effect of E2 is presumably mediated by transcriptional repression of E6 and E7 expression from the HPV-16 $P_{97}$ promoter or, e.g., in HeLA cells, from the HPV-18 p108 promoter.

By virtue of the present invention, there is provided methods and compositions for interfering with the proliferation of cells infected and/or transformed by papillomaviruses. The processes and compositions of this invention may be used to treat any mammal, including humans. According to this invention, mammals are treated by the pharmaceutically acceptable administration of an $E2_{ad/db}$ protein, either directly or by gene transfer techniques, to reduce the symptoms of the specific papillomavirus-associated disease, or to prevent their recurrence. Diseases which may be treated by the processes and compositions of this invention are those caused by the etiological agent, papillomavirus. Such diseases include, for example, epithelial malignancies, anogenital malignancies, such as cervical cancer, malignant lesions, benign lesions, papillomacarcinomas, papilloadenocystomas, papilloma neurophathicum, papillomatosis, cutaneous and mucosal papillomas, condylomas, oral, pharyngeal, laryngeal, and tongue papillomas, fibroblastic tumors and other pathological conditions associated with papillomavirus. The E2-derived compositions of this invention may also be used to treat epithelial and internal fibropapillomas in animals.

A wide variety of warts are found on human skin and are caused by the human papilloma virus (HPV). For example, the following types of warts are found on human skin and are caused by the human papilloma virus (HPV): common warts (verruca vulgaris), plantar warts, palmar warts, planar warts (verruca plana), mosaic warts, and venereal warts (condyloma accuminatum). These skin growths are unsightly, irritating, and potentially oncogenic (carcinogenic), and their removal is desired.

Genital warts, also referred to as venereal warts and condylomata acuminata, are one of the most serious manifestations of HPV infection. As reported by the Center for Disease Control, the sexual mode of transmission of genital warts is well established and the incidence of genital warts is on the increase. The seriousness of genital warts is underlined by the finding that HPV DNA can be found in all grades of cervical intraepithelial neoplasia (CIN I-III) and that a specific subset of HPV types can be found in carcinoma in situ of the cervix. Consequently, women with genital warts, containing specific HPV types are now considered at high risk for the development of cervical cancer. Current treatments for genital warts are inadequate. According to the present invention, a method of treating a patient having one or more genital warts comprises the administration of a pharmaceutical composition including an $E2_{ad/db}$ polypeptide, or a gene construct encoding the E2 protein, so as to inhibit growth of the wart. In preferred embodiments, the wart(s) are contacted directly with the pharmaceutical composition. The subject method can be used to treat, e.g, *condyloma acuminata* and/or flat cervical warts.

Laryngeal papillomas are benign epithelial tumors of the larynx. Two PV types, HPV-6 and HPV-11, are most commonly associated with laryngeal papillomas. According to the method of the present invention, laryngeal papillomas are treated administrating a pharmaceutical composition including the therapeutic E2 polypeptide, or a gene construct encoding the E2 polypeptide, so as to inhibit growth of the papillomas.

The most common disease associated with papillomavirus infection are benign skin warts. Common warts generally contain HPV types 1, 2, 3, 4 or 10. These warts typically occur on the soles of feet, plantar warts, or on the hands. Common skin warts are most often found in children and young adults. Later in life the incidence of common warts decreases presumably due to immunologic and physiologic changes. Plantar warts can often be debilitating and require surgical removal and they frequently reoccur after surgery. As above, patients suffering from common warts can be treated by the administration of a effective amount of an E2 protein according to the present invention, or a gene therapy construct which encodes the therapeutic E2 protein. In preferred embodiments, the protein or gene construct are applied, in the appropriate formulations, directly to the area of the skin afflicted with the wart(s). Similar methods and compositions may be useful in the treatment if epidermodysplasia verruciformis (EV), a rare genetically transmitted disease which is characterized by disseminated flat warts that appear as small reddish macules.

In addition, the subject method and compositions may be used to treat lesions resulting from cellular transformation for which HPV is a etiological agent, e.g., in the treatment of cervical cancer or, e.g., in the treatment of metastasized HPV positive tumors.

Accordingly, the invention has several advantages. In one embodiment, the invention may be used in the treatment of a patient infected with multiple papillomavirus subtypes without activating viral replication. Moreover, the E2 protein of one human papillomavirus subtype may functionally substitute for the E2 protein of a different viral subtype in the regulation of both viral transcription and replication (DelVecchio et al., (1992) *Am. J. Virol.* 66:5949-5958; Chiang et al., *PNAS* 89:5799-803, 1992). Thus, providing forms of E2 selected to maintain growth suppression without activating viral replication in, for example, an HPV positive lesion, e.g., a cervical carcinoma, can be expected to provide cross-protective activity in other HPV positive cells in the patient harboring entirely different viral subtypes (Dong et al., (1994) J. Virol. 68:1115-1127). The E2 residue E39 has been shown to be indispensable for the viral DNA replication function of all papillomaviruses for which it has been tested. Thus, the E39A mutation and the altered hinge mutations exemplified herein are ideal therapeutics for suppressing the growth of HPV positive cells, e.g., tumor cells or cells associated with a mixed papillomavirus infection. For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "E2 gene" or "recombinant E2 gene" refers to a nucleic acid comprising an open reading frame encoding a papillomavirus E2 polypeptide.

As used herein, the term "$E2_{ad/db}$ polypeptide" is intended to include any papillomavirus E2 polypeptide that comprises a minimal transactivation domain (i.e., activation domain or "ad") and a minimal DNA binding domain (i.e., "db") and is capable of repressing E6/E7 expression or inhibiting cell growth in papillomavirus-infected cells. Accordingly, the "$E2_{ad/db}$" may be derived from any species, e.g., bovine, human, or rabbit and any papillomavirus subtype. $E2_{ad/db}$ polypeptides also include modified $E2_{ad/db}$ polypeptides which, e.g., may have one or more alterations, e.g., amino acid substitutions (e.g., E39A), deletions, e.g., a deletion of the hinge region (e.g., BPV $E2_{220-309}$), or additions such that the polypeptide selectively suppresses cell growth in papillomavirus-infected cells in a manner superior to a corresponding unaltered wild type E2 polypeptide. Corresponding alterations may be made in other E2 polypeptides of different subtypes in order to achieve the same desired activity. Preferred $E2_{ad/db}$ polypeptides are selected for their inability to promote papillomavirus replication. In addition, preferred $E2_{ad/db}$ polypeptides are selected for there inability to repress growth in cells infected by like and non-like viral subtypes.

As used herein, the term "lacking the ability to promote papillomavirus replication" is intended to include any reduction or elimination in the ability of an $E2_{ad/db}$ polypeptide to enhance or promote papillomavirus replication as compared to the activity found in a corresponding wild type E2 polypeptide.

As used herein, the term "reduced cell growth" is intended to include any reduction in cell growth or, e.g., the complete cessation of cell growth causing, e.g., apoptosis, in one or more papillomavirus-infected cells when treated with an $E2_{ad/db}$ polypeptide or gene construct encoding such a polypeptide. Reductions in cell growth may be measured, e.g., using the colony assay as described herein.

As used herein, the term "transfection" means the introduction of a nucleic acid, e.g., an expression vector, into a recipient cell by nucleic acid-mediated gene transfer.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of an E2 gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of E2 proteins.

The term "gene construct", with respect to the subject E2 proteins, refers to a vector, plasmid, viral genome or the like which includes an E2 coding sequence, can transfect cells, preferably mammalian cells, and can cause expression of the E2 coding sequence in cells transfected with the construct. The term "gene construct" does not include a wild-type papillomavirus genome, and preferably does not include expressible coding sequences for one or more of a papillomavirus E6 or E7 proteins.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of hepatic or pancreatic origin, e.g. neuronal cells. The term also covers so-called "leaky" promoters, which regulate expression of a selected DNA primarily in one tissue, but cause expression in other tissues as well.

As used herein, the term "pharmaceutically acceptable" refers to a carrier medium which does not interfere with the effectiveness of the biological activity of the active ingredients and which is not toxic to the hosts to which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

As used herein, the term "prophylactic or therapeutic" treatment refers to administration to the host of the papillomavirus medicament. If it is administered prior to exposure to the virus, the treatment is prophylactic (i.e., it protects the host against infection), whereas if administered after infection or initiation of the disease, the treatment is therapeutic (i.e., it combats the existing infection or cancer).

As used herein the term "papillomavirus disease" refers to any kind of disease caused by the virus, including cancers and warts.

The term "cell-proliferative disorder" denotes malignant as well as nonmalignant cell populations which morphologically often appear to differ from the surrounding tissue.

Operably linked is intended to mean that the nucleotide sequence is linked to a regulatory sequence in a manner which allows expression of the nucleotide sequence. Regulatory sequences are art-recognized and are selected to direct expression of the subject papillomavirus E2 proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding papillomavirus E2 polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a peptide having an agonistic activity of a subject E2 polypeptide, or alternatively, encoding a peptide which is an antagonistic form of the E2 protein. Such expression vectors can be used to transfect cells and thereby produce polypeptides, including fusion proteins, encoded by nucleic acids as described herein.

I. Therapeutic E2 Proteins

The $E2_{ad/db}$ proteins utilized therapeutically by the present invention include both an activation domain (ad) and a DNA binding/dimerization domain (db). As described in the appended examples, the E2 transactivation and DNA binding/dimerization domains were each necessary for E2-mediated growth suppression of PV-infected and PV-transformed cells. E2 mutants which lacked a hinge region, e.g., but which retained the transactivation and DNA binding/dimerization domains, while defective in replication function nevertheless retained the ability to suppress growth of PV-transformed cells, indicating that the growth-suppressive properties of E2 can be unlinked from its DNA replication properties. As presented in the examples, an $E2_{ad/db}$ protein, i.e., E2 (E39A), having only a single lesion in the transactivation domain also had these desired characteristics.

The general structure of the papillomavirus E2 protein is well known. See, for example, McBride et al. (1991) *J. Biol Chem* 266:18411-18414; and Giri et al. (1988) *EMBO J* 7:2823-2829. Both the activation domain and the DNA binding domain of a papillomavirus E2 protein will be readily identified by one of ordinary skill in the art. For instance, a region of approximately 200 amino acids at the N terminus of E2 corresponds to the activation domain (FIG. 1). This domain contains two regions predicted to form acidic amphipathic helices (e.g., using the algorithms developed by Chou and Fasman), which have been shown to be important for the activation function of E2. DNA binding function is provided by the C-terminal 85 amino acids or so of the E2 protein (FIG. 1). Dimerization is also mediated by the DNA binding domain. The activation and DNA binding domains are recognized in human papillomavirus E2 proteins, including E2 proteins from the high risk viruses, e.g., HPV-16, -18, -31 or -33.

According to the present invention, the therapeutic E2 protein of the subject method includes both the activation and DNA binding domains. To illustrate, an exemplary $E2_{ad/db}$ protein suitable for use in the present method is generated with a human papillomavirus E2 protein, and preferably from a high risk HPV. For instance, therapeutic compositions of the present invention can be derived from an HPV-16 E2 protein and includes an activation domain corresponding to approximately Met1-Ser198 of SEQ ID No. 2 and a DNA binding domain corresponding to approximately Cys281-Ile356 of SEQ ID No. 2. Likewise, the subject method can employ an E2 protein which includes an HPV-18 E2 activation domain corresponding to approximately Met1-Asn203 and a DNA binding domain corresponding to approximately Cys282-Met365 of SEQ ID No. 4.

In a particular embodiment, the invention provides a therapeutic in the form of a modified E2 protein having an glutamic acid (E) to alanine (A) amino acid substitution at residue position 39 (e.g., HPV16 E2 (E39A)). Moreover, as this residue is conserved among many E2 proteins found in various bovine and human papillomavirus strains (e.g., BPV1, HPV6b, HPV11, HPV18, HPV31, HPV1A, and HPV57), including several high risk strains, (e.g., HPV16 and HPV18), the present invention also encompasses any corresponding mutation in any of these E2 polypeptides from any species (for a review of various species strains of papillomaviruses, see, e.g., Fields et al. (1996) *Fields Virology*). Further, such a mutation need not be an alanine substitution, but may also be any similar substitution that results in an E2 polypeptide capable of inhibiting cell growth but not capable of promoting papillomavirus replication. Accordingly, the invention encompasses a modified or altered E2 polypeptide, and methods for identifying such a polypeptide, that can repress cell growth, e.g., in papillomavirus-infected cells, but does not promote papillomavirus replication. The invention also encompasses assays for identifying E2 polypeptides having these characteristics as described herein.

The examples set forth below illustrate that the hinge region (FIG. 1), which joins the E2 polypeptide sequence between the activation and DNA binding domains, is not necessary for the growth suppressive activity of the papillomavirus E2 protein. While in preferred embodiments an intact E2 protein is utilized in the present method, e.g., a contiguous polypeptide corresponding to the activation domain, hinge region and DNA binding domain, the present invention also contemplates the use of E2 proteins which lack all or a portion of the hinge region. For example, a recombinant E2 protein can be provided in which the hinge region is deleted, the activation and DNA binding domains being directly contiguous with one and other. The examples provide the illustrative $E2_{66\ 220\text{-}309}$ protein to demonstrate the growth inhibitory activity of such constructs. Methods of making fusion proteins (or deletions as the case may be) are well known in the art. Essentially, the joining of various DNA fragments coding for different domains is performed in accordance with conventional techniques, employing blunt-ended or staggered termini for ligation, restriction enzyme digestion to provide for appropriate termini, filling-in of cohesive ends as appropriate, alkaline phosphatase treatment to avoid undesirable joining, and enzymatic ligation. In another embodiment, the $E2_{ad/db}$ gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate the $E2_{ad/db}$ gene sequence (see, for example, *Current Protocols in Molecular Biology*, eds. Ausubel et al. John Wiley & Sons: 1992).

In some instances where the hinge region has been deleted it may be desirable to introduce an unstructured polypeptide linker region between the DNA binding domain and the activation domain in place of the naturally occurring hinge region. This linker can facilitate enhanced flexibility of the protein allowing the two domains to freely and (optionally) simultaneously interact with a DNA and cellular proteins by reducing steric hindrance between the two domains, as well as allowing appropriate folding of each portion to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. Nos. 5,091,513 and 5,258,498, and can be readily incorporated by recombinant techniques.

In still other embodiments, the activation and DNA binding domains can be provided in the same molecule by chemical cross-linking. For example, there are a large number of chemical cross-linking agents that are known to those skilled in the art and useful for cross-linking the activation and DNA binding domains of an E2 protein to provide a single molecule. In an exemplary embodiment, the cross-linking agents are heterobifunctional cross-linkers which can be used to link the activation and DNA binding domains in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art. These include: succinimidyl 4-(N-maleimidomethyl) cyclohexane-1-carboxylate (SMCC), m-Maleimidobenzoyl-N-hydroxysuccinimide ester (MBS); N-succinimidyl(4-iodoacetyl)aminobenzoate (SIAB), succinimidyl 4-(p-maleimido-phenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxy-sulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate.2 HCl (DMP) are examples of useful homobifunctional cross-linking agents, and bis-[β-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in generating the subject $E2_{ad/db}$ proteins. For a recent review of protein coupling techniques, see Means et al. (1990) *Bioconjugate Chemistry* 1:2-12, incorporated by reference herein.

One particularly useful class of heterobifunctional cross-linkers, included in the representative lists above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds.

Preparing conjugates of the E2 protein domains using heterobifunctional reagents will typically be a two-step process involving the amine reaction and the sulfhydryl reaction. For the first step, the amine reaction, the E2 polypeptide sequence should contain a primary amine. This can be lysine epsilon amines or an unprotected primary α-amine found at the N-terminus. The polypeptide should not contain free sulfhydryl groups. The polypeptide chain can be modified so that all sulfhydryls are blocked using for instance, N-ethylmaleimide (see Partis et al. (1983) *J. Pro. Chem.* 2:263; and Riddles et al. (1979) *Anal. Biochem.* 94:75).

The reaction buffer should be free of extraneous amines and sulfhydryls. The pH of the reaction buffer should be 7.0-7.5. This pH range prevents maleimide groups from reacting with amines, preserving the maleimide group for the second reaction with sulfhydryls. The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

Once the reaction is completed, the first polypeptide portion of the E2 protein is now activated with a sulfhydryl reactive moiety. The activated protein may be isolated from the reaction mixture by simple gel filtration or dialysis. To carry out the second step of the cross-linking, the sulfhydryl reaction, the second E2 polypeptide portion must contain a free sulfhydryl, e.g., an unprotected cysteine residue.

Maleimides react specifically with -SH groups at slightly acidic to neutral pH ranges (6.5-7.5). A neutral pH is sufficient for reactions involving halogens and pyridyl disulfides. Under these conditions, maleimides generally react with —SH groups within a matter of minutes. Longer reaction times are required for halogens and pyridyl disulfides. The first sulfhydryl reactive-protein prepared in the amine reaction step is mixed with the second E2 polypeptide fragment under the appropriate buffer conditions. The $E2_{ad}$-$E2_{db}$ conjugates can be isolated from the reaction mixture by methods such as gel filtration or by dialysis.

Generally, where purified stocks of an E2 protein (or fragments thereof) are required, e.g., for formulation intended for direct administration, conventional recombinant techniques can be employed to express and purify an E2 protein. The term "recombinant E2 protein" refers to an E2 polypeptide of the present invention which is produced by recombinant DNA techniques, wherein generally DNA encoding an $E2_{ad/db}$ polypeptide (or discrete portions thereof) is inserted into a suitable expression vector which is in turn used to transform a host cell to produce the heterologous protein. Moreover, the phrase "corresponding to", with respect to a recombinant E2 gene, is meant to include within the meaning of "recombinant protein" those proteins having an amino acid sequence(s) of native E2 polypeptides, or an amino acid sequence similar thereto which is generated by mutations including substitutions and deletions of a naturally occurring form of an E2 protein.

For example, a host cell transfected with a nucleic acid vector directing expression of a nucleotide sequence encoding an E2 polypeptide can be cultured under appropriate conditions to allow expression of the polypeptide to occur. The E2 polypeptide may include a signal sequence and be secreted and isolated from a mixture of cells and medium containing the recombinant E2 polypeptide. Alternatively, the polypeptide may be retained cytoplasmically, as it normally is, and the cells harvested, lysed and the protein isolated. The recombinant E2 polypeptide can be isolated from cell culture medium, host cells, or both using techniques known in the art for purifying proteins including ion-exchange chromatography, gel filtration chromatography, ultrafiltration, electrophoresis, and affinity purification.

Thus, a nucleotide sequence derived from the cloning of an E2 open reading frame (ORF), encoding all or a selected portion of the full-length protein, can be used to produce a recombinant form of an E2 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known PV proteins, e.g. E6, E7 and the like. Similar procedures, or modifications thereof, can be employed to prepare recombinant E2 polypeptides by microbial means or tissue-culture technology in accord with the compositions of the subject invention.

Moreover, it is widely appreciated that fusion proteins can facilitate the expression of proteins, and accordingly, can be used in the expression of the an $E2_{ad/db}$ polypeptides of the present invention. For example, $E2_{ad/db}$ polypeptides can be generated as glutathione-S-transferase (GST-fusion) proteins. Such GST-fusion proteins can enable easy purification of the $E2_{ad/db}$ polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used at the N-terminus of the $E2_{ad/db}$ protein in order to permit purification of the poly(His)-$E2_{ad/db}$ protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

In the instance of direct delivery of a therapeutic protein (described infra), some uptake mechanisms for the protein may involve passage through lysosomes. As long half-life in the target cells is desirable, an E2 protein of this invention may be modified to increase its resistance to protease degradations and/or acid hydrolysis and, in turn, increase the half-life of the polypeptide in circulation and cells. In one embodiment of the present invention, the protease resistance of an E2 protein is increased by incorporation of D-amino acids instead of L-amino acids at some or all residues of the polypeptide, e.g., as a retro-enantio or retro-inverso peptide. In another embodiment, the peptide backbone is modified using other amide mimetics, such as trans-olefins (Shue et al. (1987) *Tetrahedron Letters* 28:3225) or phosphate derivatives (Loots et al. in *Peptides: Chemistry and Biology*, (Escom Science Publishers, Leiden, 1988, p. 118)) in order to protect the E2 protein from degradation. In still another embodiment, the amino terminus, or carboxy terminus, or both termini of an E2 polypeptide are blocked by chemical modification. In a further embodiment of this invention, lysosomal proteases are inhibited by an E2 protein in a composition comprising a lysomotrophic agent, such as chloroquine, amantadine, monensin, methylamine, or ammonium chloride.

II. Gene Therapy

In one aspect, the present invention relates to gene therapy constructs containing a nucleic acid encoding a papillomavirus $E2_{ad/db}$ polypeptide, preferably an HPV E2 protein, operably linked to at least one transcriptional regulatory sequence. The gene constructs of the present invention are formulated to be used as a part of a gene therapy protocol to deliver the subject therapeutic protein to a papillomavirus-infected or -transformed cell in an animal.

Any of the methods known to the art for the insertion of DNA fragments into a vector may be used to construct expression vectors consisting of appropriate transcriptional/translational control signals and the desired E2-encoding nucleotide sequence. See, for example, Maniatis T., Fritsch E. F., and Sambrook J. (1989): *Molecular Cloning* (*A Laboratory Manual*), Cold Spring Harbor Laboratory, Cold Spring Harbor, N.Y.; and Ausubel F. M., Brent R., Kingston R. E., Moore, D. D., Seidman J. G., Smith J. A., and Struhl K. (1992): *Current Protocols in Molecular Biology*, John Wiley & Sons, New York. These methods may include in vitro DNA recombinant and synthetic techniques and in vivo genetic recombination. Expression of a nucleic acid sequence encoding an $E2_{ad/db}$ protein may be regulated by a second nucleic acid sequence so that the protein is expressed in a host infected or transfected with the recombinant DNA molecule. For example, expression of E2 may be controlled by any promoter/enhancer element known in the art. The promoter activation may be tissue specific or inducible by a metabolic product or administered substance.

Promoters/enhancers which may be used to control the expression of the E2 gene in vivo include, but are not limited to, the native E2 promoter, the cytomegalovirus (CMV) promoter/enhancer (Karasuyama et al., 1989, *J. Exp. Med.,* 169: 13), the human β-actin promoter (Gunning et al. (1987) *PNAS* 84:4831-4835), the glucocorticoid-inducible promoter present in the mouse mammary tumor virus long terminal repeat (MMTV LTR) (Klessig et al. (1984) *Mol. Cell Biol.* 4:1354-1362), the long terminal repeat sequences of Moloney murine leukemia virus (MuLV LTR) (Weiss et al. (1985) *RNA Tumor Viruses*, Cold Spring Harbor Laboratory, Cold Spring Harbor, N.Y.), the SV40 early or late region promoter (Bernoist et al. (1981) *Nature* 290:304-310; Templeton et al. (1984) *Mol. Cell Biol.,* 4:817; and Sprague et al. (1983) *J. Virol.,* 45:773), the promoter contained in the 3' long terminal repeat of Rous sarcoma virus (RSV) (Yamamoto et al., 1980, *Cell,* 22:787-797), the herpes simplex virus (HSV) thymidine kinase promoter/enhancer (Wagner et al. (1981) *PNAS* 82:3567-71), and the herpes simplex virus LAT promoter (Wolfe et al. (1992) *Nature Genetics,* 1:379-384).

Expression constructs of the subject E2 polypeptides may be administered in any biologically effective carrier, e.g. any formulation or composition capable of effectively delivering the recombinant gene to cells in vivo. Approaches include insertion of the E2 gene in viral vectors including recombinant retroviruses, adenovirus, adeno-associated virus, and herpes simplex virus-1, or recombinant eukaryotic plasmids. Viral vectors transfect cells directly; plasmid DNA can be delivered with the help of, for example, cationic liposomes (lipofectin) or derivatized (e.g antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid into a cell is by use of a viral vector containing nucleic acid encoding the particular E2 polypeptide desired. Infection of cells with a viral vector has the advantage that a large proportion of the targeted cells can receive the nucleic acid. Additionally, molecules encoded within the viral vector, e.g., the recombinant E2 protein, are expressed efficiently in cells which have taken up viral vector nucleic acid.

One viral gene delivery system useful in the present invention utilizes adenovirus-derived vectors for in vivo expression of an E2 protein. The genome of an adenovirus can be manipulated such that it encodes and expresses a gene product of interest but is inactivated in terms of its ability to replicate in a normal lytic viral life cycle. See for example Berkner et al. (1988) *Biotechniques* 6:616; Rosenfeld et al. (1991) *Science* 252:431-434; and Rosenfeld et al. (1992) *Cell* 68:143-155. Adenoviruses (Ads) are a relatively well characterized, homogeneous group of viruses. Roughly 100 different adenoviruses, including nearly 50 serotypes isolated from humans, have been identified to date.

Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including epithelial cells (see, for example, Goldman et al. (1995) *J Virol* 69:5951-8; Clayman et al. (1985) *Cancer Gene Therapy* 2:105-111; and Rosenfeld et al. (1992), supra), including genitourinary epithelia (Bass et al. (1995) *Cancer Gene Therapy* 2:97-104). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109-127). Expression of the inserted papillomavirus E2 gene can be under control of, for example, the E1A promoter, the major late promoter (MLP) and associated leader sequences, the E3 promoter, or exogenously added promoter sequences.

Ad vectors of the present invention can be constructed by ligation of an $E2_{ad/db}$ coding sequence with adenoviral sequences contained in bacterial plasmids. See, for example, Berkner et al. (1983) *Nucleic Acids Res.* 11: 6003-6020; Haj-Ahmad et al. (1986) *J. Virol.* 57: 267-274; and Stow (1981) *J. Virol.* 37: 171-180. In a preferred strategy, two plasmids which together contain sequences comprising the entire Ad genome and the $E2_{ad/db}$ sequence are recombined. A number of conditionally defective plasmid systems have been developed making the construction of vectors simpler and reducing the number of subsequent analyses required to identify recombinant viruses. McGrory et al. (1988) *Virol.* 163: 614-617; Ghosh-Choudhury et al. (1986) *Gene* 50: 161-171; and Mittal et al. (1993) *Virus Res.* 28: 67-90. The Graham et al. PCT publication WO 95/00655, and corresponding Bett et al. (1994) *PNAS* 91:8802-8806 publication, describe a state-of-the-art set of vectors which are useful in generating adenovirus-based vectors and are particularly attractive to generating the $E2_{ad/db}$ expression constructs of the present invention.

The following properties are desirable in the design of an adenovirus vector to transfer the gene for E2 to papillomavirus-transformed cells of a patient. The vector should allow sufficient expression of the E2 protein, while producing minimal viral gene expression. There should be minimal viral DNA replication and ideally no virus replication. Finally, recombination to produce new viral sequences and complementation to allow growth of the defective virus in the patient should be minimized. An exemplary adenovirus vector encoding E2 (Ad5/E2) is described below.

Figure 2:
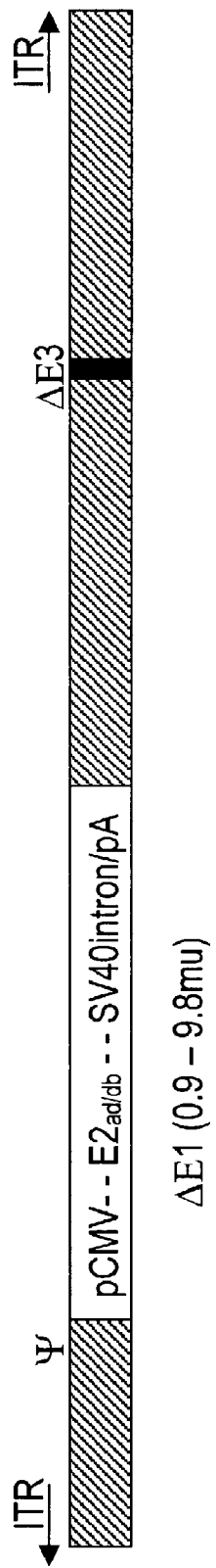
FIG. 2 is a map of an illustrative E2-encoding adenoviral vector suitable for gene therapy.

FIG. 2 is a map of an illustrative Ad5/E2 construct. This vector includes viral DNA derived from the common relatively benign adenovirus 5 serotype. The E1a and E1b regions of the viral genome, which are involved in early stages of viral replication have been deleted, as has the E3 region (though this is optional). The therapeutic papillomavirus E2 coding sequence is inserted into the viral genome in place of the E1a/E1b region (ΔE1) and transcription of the E2 sequence is driven by the human immediate early promoter region (pCMV) of the human cytomegalovirus.

Merely for illustration, the E2 ORF of a papillomavirus, such as an HPV, are amplified with primers which add HindIII and XbaI restriction sites to the 5' and 3' ends of the ORF, respectively. For example, as described by Del Vecchio et al. (1992) *J Virology* 66:5949-5958, PCR can be used to isolate HPV-16 nucleotides 2756 to 3855 (HPV-16 E2) or nucleotides 2817 to 3999 (HPV-18 E2). The amplified E2 coding sequence can then be cloned into the HindIII/XbaI site of the pCDM8 plasmid (In Vitrogen catalog V308-20) to provide the E2 coding sequence downstream of pCMV. The E2 coding sequence is also flanked at its 3' end by SV40 sequences (SV40intron/pA) which add the transcription termination and polyadenylation signals to an E2 transcript.

The resulting plasmid is linearized with SacII, and the sequence corresponding to the CMV promoter, E2 ORF and SV40intron/pA portion of the plasmid is amplified using primers which add a HindIII site at the 5' end of the CMV promoter and preserve the BamHI site at the 3' end of the SV40 sequences. The resulting PCR product, designated pCMV-$E2_{ad/db}$-SV40intron/pA, is cleaved by limited digestion with HindIII and BamHI and the appropriate fragment isolated, e.g. which includes the pCMV, E2 ORF and SV40 sequences.

The resulting HindIII/BamHI fragment is subsequently cloned into the corresponding restriction sites of the pΔE1sp1B vector (see Bett et al. (1994) *PNAS* 91:8802-8806). Following the protocols of Bett et al., the resulting shuttle vector is cotransfected into 293 cells along with, for example, the pHGG10 vector (see Bett et al., supra), and infectious particles isolated from the cell culture.

Adenoviral vectors currently in use retain most (≧80%) of the parental viral genetic material. Recently, second-generation vector systems containing minimal adenoviral regulatory, packaging and replication sequences have therefore been developed and may be used to deliver the therapeutic E2 protein. In one embodiment, the E2 protein is expressed by a pseudo-adenovirus vector (PAV). PAVs contain adenovirus inverted terminal repeats and the minimal adenovirus 5' sequences required for helper virus dependent replication and packaging of the vector. These vectors contain no potentially harmful viral genes, and may be produced in reasonably high titers and maintain the tropism of the parent virus for dividing and non-dividing human target cell types.

The PAV vector can be maintained as either a plasmid-borne construct or as an infectious viral particle. As a plasmid construct, PAV is composed of the minimal sequences from the wild type adenovirus necessary for efficient replication and packaging of these sequences and any desired additional exogenous genetic material, by either a wild-type or defective helper virus.

In one embodiment, an exemplary PAV contains adenovirus 2 (Ad2) sequences including nucleotides (nt) 0-356 of Ad2 forming the 5' end of the vector and the last 109 nt of Ad2 forming the 3' end of the construct. These sequences include the Ad2 flanking inverted terminal repeats and the 5' ITR adjoining sequences containing the known packaging signal and E1a enhancer. PCT publication WO94/12649 describes various PAVs in which convenient restriction sites have been incorporated into the fragments, allowing the insertion of E2-encoding sequences which can be packaged in the PAV virion and used for gene transfer (e.g. for gene therapy). The construction and propagation of PAV is described in detail in WO94/12649. By not containing most native adenoviral DNA, the PAVs are less likely to produce a patient immune response or to replicate in a host.

In addition, the PAV vectors can accommodate foreign DNA up to a maximum length of nearly 36 kb. The PAV vectors therefore, while especially useful for cloning larger genes can be used to transfer more than one gene, or more than one copy of the $E2_{ad/db}$ gene. For example, PAVs can be used to deliver the therapeutic E2 gene in conjunction with other genes such as p21$^{CIP1}$ or p27$^{KIP1}$.

Yet another viral vector system useful for delivery of a papillomavirus E2 gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). One advantageous feature of AAV derives from its reduced efficacy for transducing primary cells relative to transformed cells (Halbert et al. (1995) *J Virol* 69:1473). Thus, the spectrum of infectivity for a recombinant E2-derived AAV will be somewhat restricted to papillomavirus transformed cells rather than surrounding normal tissue.

Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding an E2 protein rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells (see for example, Shillitoe et al. (1994) *Cancer Gene Ther* 1:193-204; Noel et al. (1994) *Pediatr Gastroenterol Nutr* 19:43-9; Archer et al. (1995) *PNAS* 91:6840-4; Eglitis, et al. (1985) *Science* 230:1395-1398; Danos and Mulligan (1988) *Proc. Natl. Acad Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al (1989) *PNAS* 86:9079-9083; Julan et al. (1992) *J. Gen Virol* 73:3251-3255; and Goud et al. (1983) *Virology* 163:251-254); or coupling cell surface receptor ligands to the viral env proteins (Neda et al. (1991) *J Biol Chem* 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the E2 gene of the retroviral vector.

Numerous retroviral gene delivery vehicles may be utilized within the context of the present invention, including for example EP 0,415,731; WO 90/07936; WO 91/0285; WO 9403622; WO 9325698; WO 9325234; U.S. Pat. No. 5,219,740; WO 9311230; WO 9310218; Vile and Hart, *Cancer Res.* 53:3860-3864, 1993; Vile and Hart, *Cancer Res.* 53:962-967, 1993; Ram et al., *Cancer Res.* 53:83-88, 1993; Takamiya et al., *J. Neurosci. Res.* 33:493-503, 1992; Baba et al., *J. Neurosurg.* 79:729-735, 1993 (U.S. Pat. No. 4,777,127, GB 2,200,651, EP 0,345,242 and WO91/02805). For example, retroviral gene delivery vehicles of the present invention may be readily construction from a wide variety of retroviruses including for example, B, C, and D type retroviruses as well as spumaviruses and lentiviruses (see RNA Tumor Viruses, Second Edition, Cold Spring Harbor Laboratory, 1985). Briefly, viruses are often classified according to their morphology as seen under electron microscopy. Type "B" retroviruses appear to have an eccentric core, while type "C" retroviruses have a central core. Type "D" retroviruses have a morphology intermediate between type B and type C retroviruses. Such retroviruses may be readily obtained from depositories or collections such as the American Type Culture Collection ("ATCC" Rockville, Md.), or isolated from known sources using commonly available techniques.

Particularly preferred retroviruses for the preparation or construction of retroviral gene delivery vehicles of the present invention include retroviruses selected from the Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe (1976), *J. Virol.* 19:19-25), Abelson (ATCC No. VR-999), Friend, (ATCC No. VR-245), Graffi, Gross (ATCC No. VR-590), Kirsten, Harvey Sarcoma and Virus, Rauscher (ATCC NO. VR-998), and Moloney Murine Leukemia Virus (ATCC No. VR-190). Particularly preferred Rous Sarcoma Viruses include Bratislava, Bryan high titer (e.g., ATCC Nos. VR-334, VR-657, VR-726, VR-659, and VR-728), Bryan standard, Carr-Zilber, Engelbreth-Holm, Harris, Prague (e.g., ATCC Nos. VR-772, and 45033), and Schmidt-Ruppin (e.g. ATCC Nos. VR-724, VR-725, VR-354).

Any of the above retroviruses may be readily utilized in order to assemble or construct retroviral gene delivery vehicles given the disclosure provided herein, and standard recombinant techniques (e.g., Sambrook et al., *Molecular Cloning: A Laboratory Manual*, 2d ed., Cold Spring Harbor Laboratory Press, 1989; Kunkle, *PNAS* 82:488, 1985). In addition, within certain embodiments of the invention, portions of the retroviral gene delivery vehicles may be derived from different retroviruses. For example, within one embodiment of the invention, retroviral LTRs may be derived from a Murine Sarcoma Virus, at tRNA binding site from a Rous Sarcoma Virus, a packaging signal from a Murine Leukemia Virus, and an origin of second strand synthesis from an Avian Leukosis Virus.

In some embodiments, retroviral vector constructs are provided comprising a 5' LTR, a tRNA binding site, a packaging signal, one or more heterologous sequences including the E2-coding sequence, an origin of second strand DNA synthesis and a 3' LTR, but lacking gag/pol or env coding sequences. Briefly, Long Terminal Repeats ("LTRs") are subdivided into three elements, designated U5, R and U3. These elements contain a variety of signals which are responsible for the biological activity of a retrovirus, including for example, promoter and enhancer elements which are loaded within U3. LTRs may be readily identified in the provirus due to their precise duplication at either end of the genome.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with retrovirus genome into a viral particle. The tRNA is then utilized as a primer for DNA synthesis by reverse transcriptase. The tRNA binding site may be readily identified based upon its location just downstream from the 5' LTR. Similarly, the origin of second strand DNA synthesis is, as its name implies, important for the second strand DNA synthesis of a retrovirus. This region, which is also referred to as the poly purine tract, is located just upstream of the 3'LTR.

As an illustration, within one embodiment of the invention construction of retroviral vector constructs which lack gag/pol or env sequences may be accomplished by preparing retroviral vector constructs which lack an extended packaging signal. As utilized herein, the phrase "extended packaging signal" refers to a sequence of nucleotides beyond the minimum core sequence which is required for packaging, that allows increased viral titer due to enhanced packaging. As an example, for the Murine Leukemia Virus MoMLV, the minimum core packaging signal is encoded by the sequence (counting from the 5' LTR cap site) from approximately nucleotide 144, up through the Pst I site (Nucleotide 567). See, for example, the Jolly et al. PCT publication WO95/31566. The extended packaging signal of MoMLV includes the sequence beyond nucleotide 567 up through the start of the gag/pol gene (nucleotide 621), and beyond nucleotide 1040. Thus, within this embodiment retroviral vector constructs which lack extended packaging signal may be constructed from the MoMLV by deleting or truncating the packaging signal downstream of nucleotide 567.

For example, the pCDM8 plasmid described above, e.g., containing the pCMV promoter, E2 ORF and SV40intron/pA, can be used to generate the PCR product pCMV-E2 ORF-SV40intron/pA, flanked by EcoRI restriction sites. The PCR product is digested with EcoRI, and the appropriate fragment, e.g., which includes the pCMV, E2 ORF and SV40 sequences, is isolated and recloned into the MoMLV-derived pR2 vector (PCT publication WO95/31566) which has been digested at its unique EcoRI site. Modified pR2 vectors with the E2 insert in the correct orientation are isolated. The retroviral vector is electroporated into a packaging cell line, and infectious particles isolated from the cell culture.

In addition to viral transfer methods, such as those illustrated above, non-viral methods can also be employed to cause expression of a E2 polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the E2 gene by the targeted cell. Exemplary gene delivery systems of this type include liposomal derived systems, poly-lysine conjugates, and artificial viral envelopes.

In clinical settings, the gene delivery systems for the therapeutic E2 gene can be introduced into a patient by any of a number of methods, each of which is familiar in the art. For instance, a pharmaceutical preparation of the gene delivery system can be introduced systemically, e.g by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470). In preferred embodiments, the gene therapy construct of the present invention is applied topically to HPV infected or transformed cells of the skin or mucosal tissue. A papillomavirus E2 gene construct can, in one embodiment, be delivered in a gene therapy construct by electroporation using techniques described, for example, by Dev et al. ((1994) *Cancer Treat Rev* 20:105-115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

III. Pharmaceutical Preparations of E2 Protein

According to another aspect of this invention, $E2_{ad/db}$ proteins may be administered directly to PV infected cells. Direct delivery of E2 proteins may be facilitated by formulation of the protein in any pharmaceutically acceptable dosage form, e.g., for delivery intratumorally, peritumorally, interlesionally, intravenously, intramuscularly, subcutaneously, periolesionally, or (preferably) topical routes, to exert local therapeutic effects.

Topical administration of the therapeutic is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the affected cells. Successful intracellular delivery of agents not naturally taken up by cells has been achieved by exploiting the natural process of intracellular membrane fusion, or by direct access of the cell's natural transport mechanisms which include endocytosis and pinocytosis (Duzgunes (1985) *Subcellular Biochemistry* 11:195-286). Such processes are also useful in the direct delivery and uptake of the subject $E2_{ad/db}$ protein by papillomavirus-infected cells.

In one embodiment, the membrane barrier can be overcome by associating the E2 protein in complexes with lipid formulations closely resembling the lipid composition of natural cell membranes. In particular, the subject $E2_{ad/db}$ proteins are encapsulated in liposomes to form pharmaceutical preparations suitable for administration to living cells and, in particular, suitable for topical administration to human skin. The Yarosh U.S. Pat. No. 5,190,762 demonstrates that proteins can be delivered across the outer skin layer and into living cells, without receptor binding, by liposome encapsulation.

These lipids are able to fuse with the cell membranes on contact, and in the process, the associated E2 protein is delivered intracellularly. Lipid complexes can not only facilitate intracellular transfers by fusing with cell membranes but also by overcoming charge repulsions between the cell membrane and the molecule to be inserted. The lipids of the formulations comprise an amphipathic lipid, such as the phospholipids of cell membranes, and form hollow lipid vesicles, or liposomes, in aqueous systems. This property can be used to entrap the E2 protein within the liposomes.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Liposomes have been described in the art as in vivo delivery vehicles. The structure of various types of lipid aggregates varies, depending on composition and method of forming the aggregate. Such aggregates include liposomes, unilamellar vesicles, multilameller vesicles, micelles and the like, having particle sizes in the nanometer to micrometer range. Methods of making lipid aggregates are by now well-known in the art. For example, the liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

In one embodiment, pH sensitive liposomes are a preferred type of liposome for use with the present invention. One pathway for the entry of liposomes into cellular cytoplasm is by endocytosis into lysozymes of low pH. Accordingly, liposomes which are stable at neutral pH but release their contents at acidic pH can be used to deliver enzymes into the lysozymes of the cytoplasm, whereupon the contents are released.

Liposomes can be made sensitive to the low pH of the lysozymes by the lipid composition. In particular, pH sensitive liposomes can be prepared by using phospholipids which form lipid bilayers when charged but fail to stack in an ordered fashion when neutralized. An example of such a phospholipid is phosphatidylethanolamine, which is negatively charged above pH 9. The net charge of a phospholipid can be maintained at a pH which would otherwise neutralize the head groups by including charged molecules in the lipid bilayer which themselves can become neutralized. Examples of these charged molecules are oleic acid and cholesteryl hemisuccinate, which are negatively charged at neutral pH but become neutralized at pH 5. The effect of combining these together in a lipid bilayer is that at pH 9 all molecules are charged; at pH 7 the net negative charge of the oleic acid and cholesteryl hemisuccinate maintains the stability of the phosphatidylethanolamine, and at pH 5 all components are protonated and the lipid membrane is destabilized. Additional neutral molecules, such as phosphatidylcholine, can be added to the liposomes as long as they do not interfere with stabilization of the pH sensitive phospholipid by the charged molecules.

In another embodiment, the E2 polypeptide is formulated with a positively charged synthetic (cationic) lipid N-[1-(2, 3-dioleyloxy)propyl]-N,N,N-trimethylammonium chloride (DOTMA), in the form of liposomes, or small vesicles, which can fuse with the negatively charged lipids of the cell membranes of mammalian cells, resulting in uptake of the contents of the liposome (see, for example, Felgner et al. (1987) *PNAS* 84:7413-7417; and U.S. Pat. No. 4,897,355 to Eppstein, D. et al.). Another cationic lipid which can be used to generate E2-containing liposomes is the DOTMA analogue, 1,2-bis (oleoyloxy)-3-(trimethyl-ammonio)propane (DOTAP) in combination with a phospholipid to form delivery vesicles.

Lipofectin™ (Bethesda Research Laboratories, Gaithersburg, Md.) and/or LipofectAMINE™, commercially available reagents, can be used to deliver the E2 protein directly into cells. Positively charged complexes prepared in this way spontaneously attach to negatively charged cell surfaces, fuse with the plasma membrane, and can efficiently deliver functional E2 protein into, for example, keratinocytes. Sells et al. (1995) *Biotechniques* 19:72-76 describe a procedure for delivery of purified proteins into a variety of cells using such polycationic lipid preparations.

A significant body of information is emerging regarding the use of other cationic lipids for the delivery of macromolecules into cells. Other suitable lipid vesicles for direct delivery of the E2 protein include vesicles containing a quaternary ammonium surfactant (Ballas et al. (1988) *Biochim. Biophys Acta* 939:8-18); lipophilic derivatives of spermine (Behr et al. (1989) *PNAS* 86:6982-6986).

The lipid formulations of the subject E2 protein can be used in pharmaceutical formulations to deliver the E2 protein by various routes and to various sites in the animal body to achieve the desired therapeutic effect. Local or systemic delivery of the therapeutic agent can be achieved by administration comprising application or insertion of the formulation into body cavities, inhalation or insufflation of an aerosol, or by parenteral introduction, comprising intramuscular, intravenous, intradermal, peritoneal, subcutaneous and topical administration.

Topical formulations are those advantageously applied to the skin or mucosa. Target mucosa can be that of the gastrointestinal tract, comprising the mouth, larynx, esophagus and stomach, or the vaginal, vulvar, penal or anorectal mucosa. Other target tissues can be the accessible epidermal tissues which are infected by HPV. Lipids present in topical formulations can act to facilitate introduction of therapeutic E2 protein into the target tissue, such as the stratum or corneum of the skin, by perturbing the barrier properties of the protective membrane, or by introducing perturbing agents or penetration enhancers such as Azone™ or by promoting the activity of these penetration enhancers.

Other pharmaceutical formulations comprising the cationic lipids of the invention are topical preparations containing an anesthetic or cytostatic agent, immunomodulators, bioactive peptides or oligonucleotides, sunscreens or cosmetics. Preparations for topical use are conveniently prepared with hydrophilic and hydrophobic bases in the form of creams, lotions, ointments or gels; alternatively, the preparation may be in the form of a liquid that is sprayed on the skin. The effect of the cationic lipids is to facilitate the penetration of the active antiviral agent through the stratum corneum of the dermis.

The composition and form of pharmaceutical preparations comprising the liposome, in combination with the E2 protein, can vary according to the intended route of administration.

Also, by suitable modifications of the liposome membranes, the liposomes can be made to bind to specific subpopulations of cells.

In still another embodiment, the therapeutic E2 protein can be delivered by way of an artificial viral envelope (AVE). Briefly, the art as described a number of viral envelopes which exploit molecular recognition of cell surface receptors by viral surface proteins as a means for selective intracellular delivery of macromolecules, including proteins. According to the method of Schreier, et. al., U.S. Pat. No. 5,252,348, a virtually unlimited number of artificial viral envelopes can be prepared and applied using recombinant or isolated surface determinants. For example, the AVEs be generated as viral mimetics of a number of human viruses including arboviruses; flaviviridae; bunyaviridae; hepatitis viruses; Epstein-Barr viruses; herpes viruses; paramyxoviruses; respiratory syncytial virus; retroviruses including human T-lymphotrophic virus type I and II (HTLV-I/II) and human immunodeficiency virus type 1 and 2 (HIV-1/2); rhinoviruses; orthopoxviruses; and human papilloma viruses.

In another embodiment, direct delivery of a therapeutic E2 protein may be facilitated by chemical modification of the polypeptide itself. One such modification involves increasing the lipophilicity of the E2 protein in order to increase binding to the cell surface, in turn, stimulating non-specific endocytosis of the protein. Lipophilicity may be increased by adding a lipophilic moiety (e.g., one or more fatty acid molecules) to the E2 protein. A wide variety of fatty acids may be employed. For example, the protein may be palmitoylated. Alternatively, a lipopeptide may be produced by fusion or cross-linking, to permit the E2 protein to resemble the natural lipopeptide from *E.coli,* tripalmitoyl-S-glycerylcysteil-seryl-serine, at its amino terminus. This lipopeptide has been shown to increase the uptake of fused peptides (P. Hoffmann et al., (1988) *Immunobiol.* 177:158-70). Lipophilicity may also be increased by esterification of the protein at tyrosine residues or other amino acid residues. And uptake of the E2 protein may be increased by addition of a basic polymer such as polyarginine or polylysine (Shen et al. (1978) *PNAS* 75:1872-76).

Direct delivery of E2 proteins according to this invention may also be effected by the use of transport moieties, such as protein carriers known to cross cell membranes. For example, an E2 protein may be fused to a carrier protein, preferably by a genetic fusion which may be expressed in a system such as *E.coli* or yeast. According to one embodiment of this invention, the amino terminus of the E2 protein may be fused to the carboxy terminus of a transport moiety using standard techniques.

Nucleotide sequences encoding such carrier-E2 protein fusion proteins, operatively linked to regulatory sequences, may be constructed and introduced into appropriate expression systems using conventional recombinant DNA procedures. The resulting fusion protein may then be purified and tested for its capacity to (1) enter intact eukaryotic cells and (2) inhibit E2-dependent gene expression and viral DNA replication once inside the intact eukaryotic cells.

In choosing a useful carrier protein, those of skill in the art will recognize the desirability of appropriate control experiments designed, inter alia, to test the possibility that the carrier portion of the fusion protein itself interacts with elements of the E2 transcriptional regulation system. If the carrier portion of the fusion protein is found to have undesirable interactions, such as activation of E2-dependent enhancer elements, the portions of the carrier sequence responsible for these interactions should be identified and deleted in a way which permits the sequence to retain its carrier capacity. Alternately, one of several conventional carrier sequences which do not interact with elements of the E2 transcriptional regulation system can be substituted.

Useful carrier proteins include, for example, bacterial hemolysins or "blending agents", such as alamethicin or sulfhydryl activated lysins. Other carrier moieties which may be used include cell entry components of bacterial toxins, such as Pseudomonas exotoxin, tetanus toxin, ricin toxin, and diphtheria toxin. Also useful is melittin, from bee venom. Other useful carrier proteins include proteins which are viral receptors, cell receptors or cell ligands for specific receptors that are internalized, i.e., those which cross mammalian cell membranes via specific interaction with cell surface receptors, recognized and taken into the cell by cell surface receptors. Such cell ligands include, for example, epidermal growth factor, fibroblast growth factor, transferrin and platelet-derived growth factor. Alternatively, the ligand may be a non-peptide, such as mannose-6-phosphate, which permits internalization by the mannose-6-phosphate receptor. The transport moiety may also be selected from bacterial immunogens, parasitic immunogens, viral immunogens, immunoglobulins or fragments thereof that bind to target molecules, cytokines, growth factors, colony stimulating factors and hormones. A transport moiety may also be derived from the tat protein of HIV-1.

As an alternative or addition to the above-described chemical modifications and protein carriers, which may be employed alone or in combination, other agents which allow penetration of the keratinized cell layer may be employed to facilitate delivery of the E2 proteins of this invention to papillomavirus-infected cells. In topical applications, for example, the E2 protein may be administered in combination with dimethylsulfoxide, an agent which promotes penetration of cell membranes by substances mixed with it. Useful keratinolytic agents include, for example, salicylic acid, urea, and alpha -hydroxyacids. For such applications, the E2 protein and any other agent may be administered topically, in cream or gel form.

According to an alternate embodiment of this invention, the therapeutic E2 protein may be administered serially or in combination with other therapeutics used in the treatment of papillomavirus infections or diseases caused by them. Such therapeutics include interferons, such as IFN-$\gamma$, IFN-$\alpha$ and IFN-$\beta$ derived from natural sources or produced by recombinant techniques, other cell mediators formed by leukocytes or produced by recombinant techniques such as for example, interleukin-1, interleukin-2, tumor necrosis factor, macrophage colony stimulating factor, macrophage migration inhibitory factor, macrophage activation factor, lymphotoxin and fibroblast growth factor. Alternatively, the E2 protein may be administered serially or in combination with conventional therapeutic agents or regimens such as, for example, salicylic acid, podophyllotoxin, retinoic acid, surgery, laser therapy and cryotherapy. Such combination therapies may advantageously utilize less than conventional dosages of those agents, or involve less radical regimens, thus avoiding any potential toxicity or risks associated with those therapies.

It will also be understood by those skilled in the art that any of the above enumerated delivery methods may be augmented, where topical application is being carried out, by the use of ultrasound or iontophoretic delivery devises which facilitate transdermal delivery of proteins. See, for example, Banga et al. (1993) *Pharm Res* 10:697-702; and Mitragotri et al. (1995) *Science* 269:850-853.

Exemplification The invention now being generally described, it will be more readily understood by reference to the following examples which are included merely for purposes of illustration of certain aspects and embodiments of the present invention, and are not intended to limit the invention.

Carcinogenic progression of a human papillomavirus (HPV)-infected cell is often associated with integration of the viral genome in a manner which results in the loss of expression of the viral regulatory protein E2. One function of E2 is the regulation of expression of the viral oncogenes, E6 and E7. Introduction of the bovine papillomavirus type 1 (BPV-1) E2 transactivator (E2-TA) in HeLa cells, an HPV type 18 (HPV-18)-positive cervical carcinoma cell line results in growth arrest. In this study, we have found that the HPV-16 and HPV-18 E2 proteins share with BPV-1 E2-TA the ability to suppress HeLa cell growth. This property was not observed for the BPV-1 E2 transcriptional repressor (E2-TR). Analysis of various mutant E2 proteins for growth suppression revealed a requirement for the intact transactivation and DNA binding domains. A HeLa cell line (HeLa-tsE2) which expressed a conditional mutant E2 protein that was functional only at the permissive temperature (32° C.) was established, permitting an analysis of the molecular and cellular consequences of E2 expression. Our data indicates that one mechanism by which E2 suppresses cellular growth is through repression of E6 and E7 expression, thereby enabling the cellular targets of E6 and E7 to resume regulation of the cell cycle.

The functions of the E2 proteins have been extensively characterized for BPV-1. The BPV-1 E2 ORF encodes three different proteins: an internally initiated E2 transcriptional repressor (E2-TR), a spliced product between E8 and E2 (E8-E2), and the E2 transactivator (E2-TA) (Hubbert et al. (1988) Proc. Natl. Acad. Sci. USA, 85:5864-5868; Lambert et al. (1989) J. Virol., 63:3151-3154). The full-length E2 protein (E2-TA) can function as a transactivator or a repressor, depending on the location of E2 binding sites in a responsive promoter. It has two functional domains which are well conserved among the E2 proteins of different papillomaviruses (Giri and Yaniv (1988) EMBO J., 7:2823-2829; McBride et al. (1991) J. Biol. chem., 266:18411-18414), a 200-amino-acid transactivation domain at the N terminus and a 90- to 100-amino-acid C-terminal domain that is essential for dimerization and DNA binding (Li et al. (1989) Genes Dev., 3:510-526; McBride et al. (1989) Proc. Natl. Acad. Sci. USA, 86:510-514, McBride et al. (1988) EMBO J., 7:533; Moskaluk and Bastia (1988) J. Virol., 62:1925-1931). A flexible spacer region called "the hinge" separates the transactivation and DNA binding domains. Both E2-TR and E8-E2 can inhibit the transactivation function of the full-length protein, through mechanisms that may involve competition with E2-TA for DNA binding or by subunit mixing and heterodimer formation with the full-length protein. E2-TA can directly repress transcription of promoters in which the E2 binding sites are located near essential promoter elements such as the TATA box or SP1 binding sites (Dostatni et al. (1991) Genes Dev., 5:1657-1671; Gloss and Bernard (1990) J. Virol., 64:5577-5584; Matsushime et al. (1994) Mol. Cell Biol., 14:2066-2076; Li et al. (1991) Cell 65:493-505, Romanczuk et al. (1990) J. Virol., 64:2849-2859; Spalholz et al. (1991) J. Virol., 65:743-753; Thierry and Howley (1991) New Biol., 3:90-100; Vande Pol and Howley (1990) J. Virol., 64:5420-5429). In these cases, E2-TA is believed to interfere with the assembly of the transcriptional initiation complex.

The studies presented here were designed to examine the effect of E2 expression in cervical carcinoma cell lines. We were able to confirm earlier studies showing that expression of BPV-1 E2-TA results in growth suppression of HeLa cells. However, we found that (i) the expression of HPV E2 proteins specifically inhibited PV-infected and PV-transformed cells, as opposed to the non-specific inhibition by BPV E2 proteins shown in the art, and (ii) the E2-TR protein was unable to suppress cellular growth. Using a series of mutated E2 proteins, were able to determine which domains of the E2 protein were important for this activity. We were also able to demonstrate that HPV-16 and HPV-18 E2 proteins had similar growth suppression functions and these proteins must maintain transcriptional activation function in order to retain this growth suppression function although transcriptional activation function alone is not sufficient (e.g, VP16 E2). Establishment of a HeLa cell line allowed further characterization of E2-mediated growth suppression. These studies indicate that at least one consequence of E2 expression in HPV-positive cell lines is decreased expression of the viral oncoproteins, resulting in cell cycle arrest.

Finally, these studies also exemplify the preparation and isolation of two different altered E2 polypeptides from two different strains of papillomavirus, i.e., bovine and human, that have the advantage of being able to suppress cell growth without triggering undesired papillomavirus replication.

Materials and Methods

Recombinant plasmids: The plasmids used for expression of the various BPV-1 E2 proteins were based on C59, which utilizes the SV40 early promoter to express the full-length E2 protein (Spalholz et al. (1991) J. Virol., 65:743-753; Yang et al. (1985) Nature (London) 318:575-577). The C59-derived E2-TA plasmid used in this study has been modified to contain a Kozak initiation consensus sequence (CCACCATG [Kozak, M. (1991) J. Biol. Chem., 266:19867-19870]) as previously described (Winokur and McBride (1992) EMBO J., 11:4111-4118). The plasmids used for expression of E2-TR and the E2-TR with the translation termination linker in E5 (p1175) were previously described (Lambert et al. (1987) Cell 50:68-78). Plasmids which express the E2 mutant proteins $E2_{>1-15}$, $E2_{>157-282}$, $E2_{>220-309}$ (McBride et al. (1989) Proc. Natl. Acad. Sci. USA, 86:510-514; Winokur and McBride (1992) EMBO J., 11:4111-4118), and $E2_{1-218}$ have been previously described (Yang et al. (1985) Nature (London) 318:575-577). Plasmids that express E2 mutant proteins $E2_{(E39A)}$ and $E2_{(I73A)}$ were constructed as described in Sakai et al. (1996) J. Virology 70:1602-1611.

ts E2 was subcloned from plasmid pE2ts-1 (DeMaio and Settleman (1988) EMBO J., 7:1197-1204) by PCR using oligonucleotides containing a HindIII site at the 5' end and an XbaI site at the 3' end of the E2 gene. Pfu polymerase (from Stratagene) was used to ensure high fidelity. The DNA fragment containing temperature-sensitive E2 (tsE2) was cloned into the vector pRC-CMV (Invitrogen) at the HindIII-XbaI sites of the polylinker. This vector also contains the gene for neomycin resistance. The sequence of this clone was verified by automated DNA sequence analysis (ABI model 373A sequencer). The mutant E2 gene contains an insertion of the four-amino-acid sequence Pro-Arg-Ser-Arg between amino acids 181 and 182 (DeMaio and Settleman (1988) EMBO J., 7:1197-1204).

Cell culture: HeLa, HT-3, SiHa, Caski, and C33A are human cervical cancer cell lines obtained from the American Type Culture Collection that have been previously analyzed for the presence of HPV DNA and HPV RNA (Yee et al. (1985) Am. J. Pathol., 119:361-366). Saos-2, a human osteosarcoma cell line, was obtained from Phil Hinds (Harvard Medical School). An immortalized human foreskin keratinocyte cell line (W16) was immortalized by using the full-length genome of HPV-16 linearized with BamHI, as previously described (Romanczuk and Howley (1992) Proc. Natl. Acad. Sci. USA, 89:3159-3163).

HeLa, SiHa, Caski, C33A, and Saos-2 cells were maintained in Dulbecco modified Eagle medium with 10% fetal bovine serum. HT-3 cells were maintained in McCoy's 5A medium (Gibco/BRL) with 10% fetal bovine serum. The HPV-16-immortalized Keratinocyte line (W16) was maintained in 3+1 medium (3 parts KGM plus 1 part Dulbecco modified Eagle medium).

Growth suppression assay. Cells were seeded at $1\times10^6$ to $2\times10^6$ cells per 10-cm-diameter dish the day before transfection. Cells were transfected by lipofection (Lipofectin; GIBCO BRL), using 8 to 10 µg of plasmid DNA purified through two CsCl gradient centrifugations per 10-cm-diameter plate. Sixteen hours after transfection, cells were referred; at 24 h posttransfection, the cells were split and placed under selection in medium containing 10% fetal bovine serum and G418 (concentration dependent on the cell line). Cells were maintained under selection for 2 to 3 weeks until the number of drug-resistant colonies could be determined. Cells were fixed in 10% formaldehyde for 15 min. washed, and stained with methylene blue for 15 min. Plates were washed, and G418-resistant colonies were counted.

Chloramphenicol acetyltransferase assays: Reporter plasmid was cotransfected into HeLa cells (Chen and Okayama (1987) *Mol. Cell Biol.*, 7:2745-2752) with the indicated expression plasmids (empty vector was used to normalize the amount of total DNA transfected) by the calcium phosphate method. At 48 h after transfection, cells were harvested and lysed in 250 mM Tris (pH 8.0), and chloramphenicol acetyltransferase activity was determined (Gorman et al. (1982) *Mol. Cell Biol.*, 2:1044-1051).

Replication Assay: Transient replications of HPV16 origin-containing plasmid p16Ori were analyzed essentially by the technique previously described by Del Vecchio et al. (Del Vecchio et al. (1992) *J. Virol.* 66:5949-5958). At 70 h after transfection, low-molecular weight DNA was extracted by the method of Hirt, (Hirt, (1967) *J. Mol. Biol.* 26:365-369) modified as described below. Plates were washed two times with phosphate-buffered saline without magnesium or calcium. The cells were then scraped into a 1.5-ml tube, pelleted, resuspended in 200 µl of buffer 1 (50 mM glucose, 25 mM Tris-HCl [pH 8.0], 10 mM EDTA, 100 mg of RNase A per ml), and lysed by the addition of 200 µl of buffer II (1% SDS, 0.2 N NaOH). After 5 min, 200 µl of ice-cold buffer III (3 M to 5 M potassium acetate) was added, and the samples were placed at 4° C. for at least 1 h. After centrifugation for 10 min at 4° C., they were extracted once with buffer-saturated phenol and once with phenol-chloroform-isoamyl alcohol and precipitated with ethanol. To distinguish replicated DNA from input DNA, the extracted DNA samples were digested with DpnI. (Plasmid DNA was prepared from a Dam methylase-positive bacterial strain, rendering it sensitive to DpnI digestion.) To linearize p16Ori, the sample DNAs were also digested with XmnI. The digested samples were separated by 1.0% agarose gel electrophoresis and then analyzed by Southern blotting. The alkaline transfer to Hybond–N+ membranes (Amersham) was performed by the manufacturer's method. A DNA fragment encompassing the origin sequence and lacZ coding sequence was generated for use as a probe by PCR with the p16Ori template. This fragment was labeled by using a random-primed labeling kit (Stratagene). Hybridization in 50% formamide-containing buffer and subsequent washes were done by standard methods (Sandler, et al. (1993) *J. Virol.* 67:5079-5087). The sample DNA digested with DpnI and XmnI was also subjected to PCR-southern blot analysis. To amplify DpnI digestion-resistant (replicated) DNA, primers (nt 1814 to 1843 and 2628 to 2657 of pKS(-) BluescriptII; Strategene; GenBank accession number X52329) were used with 10 cycles of PCR amplification. There are nine DpnI sites within the sequence amplified with these primers. The amplified DNA was analyzed by Southern blotting. A Phosphor-Imager (Bio-Rad Laboratories) was used for quantitation of the hybridized signals. The amount of the template DNA for amplification was confirmed to be within the quantitative range (input DNA=0.1 to 50 pg).

Generation of HeLa-ts E2 cell line: ts E2 was linearized with BglII and transfected into HeLa cells by lipofection. Transfected cells containing ts E2 were selected for in 450 µg of G418 per ml. and individual colonies were analyzed.

RNA analysis: The HeLa-tsE2 cell line and the control cell line containing the vector alone (HeLa-V) were split, and $10^6$ cells were plated. Cultures were at maintained at 32 or 38° C. for 5 days. Total RNA was harvested by using a Biotex RNA isolation kit. Total RNA (14 µg) was separated by 1.2% agarose-formal-dehyde gel electrophoresis for Northern (RNA) blot analysis. The RNA was transferred to a GeneScreen Plus filter and hybridized with a probe for HPV-18 E6/E7 mRNA levels and with the cyclophilin probe (Danielson et al. (1988) *DNA*, 7:261-267).

Immunological procedures: For immunoblotting, cell lysates were prepared in lysis buffer (0.1 M NaCl, 2mM EDTA, 20 mM Tris [pH 8.0], 1% Nonidet P-40, per ml, 5 mM sodium fluoride, 1 mM sodium orthovanadate) on ice for on ice for 30 min. Lysates were cleared by centrifugation at 15,000×g at 4° C. for 5 min. A 100 µg aliquot of protein from the cell lysate of each sample was separated by sodium dodecyl sulfate-polyacrylamide gel electrophoresis (SDS-PAGE) followed by immunoblotting (Towbin et al. (1979) *Proc. Natl. Acad. Sci. USA*, 86:4350-4354). The protein concentrations were determined by the Bio-Rad protein assay. Monoclonal antibody 1801 (Ab-2 from Oncogene Science) was used for p53 detection. Monoclonal antibody 245 (PharMingen) was used for pRb detection. Mouse monoclonal antibody sdi-1p21 (1509-A; PharMingen) was used for p21/WAF1/C1p1 detection. Horseradish peroxidase-conjugated rabbit anti-mouse antibody (NA 931; Amersham) was used, followed by enhanced chemiluminescence detection (Renaissance system; NEN).

Immunocomplex kinase assays: Immunoprecipitations were carried out essentially as described previously (Matsushime et al. (1994) *Mol. Cell Biol.*, 14:2066-2076), using 100 µg of cellular extract. Rabbit polyclonal antibody C-8 (Santa Cruz) was used to precipitate cyclin A. Mouse monoclonal antibody HE-111 (Santa Cruz) was used to precipitate cyclin E complexes.

Kinase assays were carried out as described previously (Matsushime et al. (1994) *Mol. Cell Biol.*, 14:2066-2076), using histone H1 as a substrate. Proteins were separated by SDS-PAGE (11% polyacrylamide gel). Coomassie blue stained, and dried, and phosphorylated proteins were visualized by autoradiography.

Results (i) Suppression of HeLa Cell Growth by BPV-1 E2-TA but Not E2-TR.

Expression of the full-length BPV-1 E2-TA protein in HeLa cells results in suppression of cell growth as assayed by a reduction in colony formation (Thierry and Yaniv (1987) *EMBO J.*, 6:3391-3397). We believe that the decreased expression of the viral oncoproteins may contribute to this growth suppression, since expression of the full-length E2 proteins of BPV-1, HPV-16, and HPV-18 as well as HPV-18C (an artificially truncated HPV-18 E2 repressor construct, analogous to BPV-1 E2-TR) is capable of down regulating transcription from the HPV-18 $P_{105}$ promoter (Thierry and Howley (1991) *New Biol.*, 3:90-100). Furthermore, growth suppression of HeLa cells by BPV-1 E2-TA expressed from an SV40-based vector results in the down regulation of E6 and E7 expression from the viral $P_{105}$ promoter (Hwang et al. (1993) *J. Virol.*, 67:3720-3729).

To further investigate the mechanisms involved in the E2 regulation of cellular proliferation, we examined whether BPV-1 E2-TR could suppress HeLa cell growth like the full-length BPV-1 E2-TA. HeLa cells were cotransfected with a plasmid conferring neomycin resistance (pSV2neo) and a plasmid encoding either BPV-1 E2-TA or BPV-1 E2-TR. Cells were split after transfection and maintained in G418-containing medium for 14 to 21 days, at which time the number of G418-resistant colonies was determined. No growth suppression was observed with BPV-1 E2-TR (FIG. 1). Since the E2-TR plasmid used in this experiment contains an intact E5 gene which might mask or otherwise affect a growth-suppressive effect of E2-TR, an E2-TR construct (p1175) with a translation termination linker in E5 was tested and also found to be defective for HeLa cell growth suppression. Similar results were obtained when puromycin selection rather G418 selection was used, indicating that these results were not specific for neomycin resistance selection.

The lack of growth suppression by E2-TR was unexpected, since E2-TR has been shown to specifically repress E2-responsive promoters. To confirm that E2-TR was indeed expressed in HeLa cells, the E2-TR plasmid was tested for its ability to repress E2-TA transactivation in HeLa cells. HeLa cells were transfected with the E2-TA plasmid, the E2-responsive plasmid 6XE2TKCAT (Thierry et al. (1990) *Mol. Cell Biol.*, 10:4431-4437), and increasing amounts of the E2-TR plasmid. We observed that E2-TR was able to specifically repress E2-TA transactivation, indicating expression of functional E2-TR in HeLa cells.

(ii) HPV-16 and HPV-18 E2 Proteins Suppress Cell Growth in HeLa Cervical Carcinoma Cells.

The abilities of HPV-16 and HPV-18 E2 proteins to suppress HeLa cell growth were next examined. In this series of experiments, we tested whether the E2 proteins of the high-risk HPVs shared the growth-suppressive function shown for the BPV-1 E2-TA protein. The experiment was performed with HPV-16 E2 and HPV-18 E2 expression plasmids that had been previously shown to express functional E2 protein capable of supporting origin-dependent DNA replication and of activating E2-responsive promoters (Del Vecchio et al. (1992) *J. Virol.*, 66:5949-5958). Both HPV-16 E2 and HPV-18 E2 proteins suppressed HeLa cell growth in the colony formation assay (Table 1). This result differs from a previous report that expression of HPV-18 E2 was not able to suppress the growth of HeLa cells (Thierry and Yaniv (1987) *EMBO J.*, 6:3391-3397).

TABLE 1

HeLa cell growth suppression by HPV-16 and HPV-18 E2[a]

| Transfection | No. of G418-resistant colonies[b] | |
|---|---|---|
| | Expt. 1 | Expt. 2 |
| HPV-16 E2 | 0 | 0 |
| HPV-18 E2 | 0 | 0 |
| Vector alone | 34 | 41 |

[a]HeLa cells were transfected with 1 µg of pSV2neo and 10 µg of either HPV-16 E2- or HPV-18 E2-expressing plasmid or vector alone.
[b]Transfected cells were maintained under selection in medium containing 500 µg of G418 per ml for 2 to 3 weeks, and the number of G418-resistant colonies from each transfection was determined.

(iii) Growth Suppression Mediated by E2 is Observed in Other HPV-Positive Cell Lines.

To examine the specificity of E2 growth suppression, additional cell lines were assayed for their responses to E2 expression using the colony reduction assay. E2 growth suppression was observed in each of the three HPV-positive cell lines tested in which the viral genes are expressed from the viral long control region. These include two HPV-16-positive cervical carcinoma cell lines. SiHa and Caski, and W16, which is a human foreskin keratinocyte cell line immortalized by HPV-16 (Table 2). Growth suppression by BPV-1 E2-TA was observed in each of these cell lines, and no growth suppressive effect was observed with the BPV-1 E2-TR protein. These data are in agreement with the results of Hwang et al. (Hwang et al. (1993) *J. Virol.*, 67:3720-3729), who also reported growth suppression of other HPV-positive cervical cancer cell lines by BPV-1 E2-TA.

TABLE 2

BPV-1 E2 growth suppression of HPV-16-expressing human cell lines[a]

| | No. of G418-resistant colonies | | | | | |
|---|---|---|---|---|---|---|
| | SiHa | | Caski | | W16 | |
| Transfection | Expt. 1 | Expt. 2 | Expt. 1 | Expt. 2 | Expt. 1 | Expt. 2 |
| E2-TA | 6 | 4 | 2 | 0 | 4 | 8 |
| E2-TR | 52 | 42 | 59 | 67 | 18 | 19 |
| Vector alone | 46 | 57 | 51 | 55 | 24 | 23 |

[a]Indicated cell lines were transfected with 1 µg of pSV2neo and 10 µg of either BPV-1 E2-TA- or BPV E2-TR-expressing plasmid or vector alone.

To determine whether E2 can act as a general growth suppressor, two cervical carcinoma cell lines which are HPV negative (C33A and HT-3) and a human osteosarcoma cell line (Saos-2) were tested for growth suppression by E2-TA. It was previously reported that E2-TA could suppress the growth of HT-3 cells when introduced by infection with an E2-expressing recombinant SV40 (Hwang et al. (1993) *J. Virol.*, 67:3720-3729). In our assay, however, the growth of each of these HPV-negative cell lines, including HT-3, was unaffected by expression of the E2-TA protein (Table 3). Thus, the E2 growth suppression in the colony reduction assay is specific for HPV-positive cells.

TABLE 3

Lack of BPV-1 E2 growth suppression of HPV-negative human cell lines[a]

| | No. of G418-resistant colonies | | |
|---|---|---|---|
| | Saos-2 | | |
| Transfection | Expt. 1 | Expt. 2 | HT-3 |
| E2-TA | 67 | 80 | 24 |
| E2-TR | 81 | 102 | 28 |
| Vector alone | 62 | 99 | 19 |

[a]See the footnote to Table 2. For C33A cells, values were >500 in all assays in two experiments.

(iv) Intact DNA Binding and Transactivation Functions of the E2 Protein are Required for Inhibition of HeLa Cell Growth.

The domains of BPV-1 E2 necessary for growth suppression were mapped by using a series of truncation and deletion mutants of E2, which had been previously characterized for their transactivation and replication functions (Winokur and McBride (1992) *EMBO J.*, 11:4111-4118). The growth-suppressive phenotype conferred by the E2 deletion mutants was assayed in HeLa cells by using the colony reduction assay (FIG. 3A). Growth suppression was observed with E2-TA and with $E2_{>220-309}$, which is a mutant deleted of a large segment of the hinge region but containing an intact transactivation domain and an intact DNA binding/dimerization domain. No growth suppression was observed for either $E2_{>1-15}$ or $E2_{>157-220}$, both of which are deficient for the transcriptional transactivation and DNA replication functions in mammalian cells. Each of these E2 mutants can inhibit the transactivation properties of E2-TA in trans. An E2 mutant protein ($E2_{1-218}$) consisting of only the transactivation domain similarly had no negative effect on cell growth. The E2$_{>220-309}$ mutant, which has growth-suppressive activity, is able to transactivate an E2-responsive plasmid but is defective in origin-dependent DNA replication (Winokur and McBride (1992) *EMBO J.*, 11:4111-4118). We confirmed the transactivation or transrepression properties of each of these mutant E2 proteins in HeLa cells. The expression of the E2 proteins was demonstrated in COS cells by immunoblotting, using expression from recombinant PAVA viruses. In these studies, it was noted that the E2$_{1-218}$ mutant was expressed at a somewhat lower level than the other E2 proteins. These results indicate that the BPV-1 E2 growth-suppressive effect in HeLa cells requires a functional transactivation domain as well as an intact DNA binding domain but that an intact DNA replication function is apparently not necessary.

The genetic organization of BPV-1 is complex, with overlapping ORFs at the 3' end of the early region, raising the possibility that another ORF contributes to the growth suppression phenotype. This, however, is quite unlikely. The intact E2-TA expression vector that was used contains additional ORFs, including E3 (3267 to 3551), E4 (3173 to 3526), and E5 (3714 to 4010). The E2$_{>220-309}$ deletion mutant plasmid, which expresses an E2 capable of growth suppression, is deleted of most of the coding regions of E3 and E4 (from 3265 to 3532 of the BPV-1 genome). Furthermore, E5 has been previously shown not to be associated with the growth-suppressive effect observed with the BPV-1 E2 expression vector (Thierry and Yaniv (1987) *EMBO J.*, 6:3391-3397). Thus, we conclude that the growth-suppressive phenotype can be attributed to E2.

We next examined the specificity of the E2 transactivation domain in suppressing HeLa cell proliferation by testing whether this function could be provided by other acidic activation domains. Chimeric constructs containing the E2 DNA binding/dimerization domain fused to either the acidic transactivation domain of the herpesvirus VP16 transcriptional activator or the spi oncogene (Gauthier et al. (1993) *EMBO J.*, 12:5089-5096) were tested in the colony reduction assay (FIG. 3B). Although both chimeric proteins were able to efficiently transactivate E2-responsive reporter constructs in HeLa cells, neither had the ability to suppress HeLa cell proliferation. This finding indicates that the ability of the E2 transactivation domain to suppress cellular proliferation is specific and not due to its general transactivation property.

The dimerization and DNA binding properties of BPV-1 E2 have been separated by point mutations in the DNA binding domain (Barsoum et al. (1992) *J. Virol.*, 66:3941-3945; McBride et al. (1989) *J. Virol.*, 63:5076-5085). E2 mutants that can dimerize but not bind DNA and that can no longer dimerize or bind DNA have been described. Two of these E2 mutants were tested for the ability to suppress HeLa cell growth. Neither the E2$_{(I331R)}$ mutant, which is defective for both dimerization and DNA binding, nor the E2$_{(R344K)}$ mutant, which can dimerize but not bind DNA, was capable of suppressing HeLa cell proliferation (FIG. 3B). These results suggest that both the E2 transactivation and DNA binding functions are necessary for the E2 growth suppression phenotype.

(v) Molecular Consequences of E2 Expression.

To study the downstream effects of E2 expression in HPV-positive cells, we used a conditional BPV-1 E2 mutant that has normal replication and transactivation functions at 32° C. which are inactivated at either 37 or 39° C. (DiMaio and Settleman (1988) *EMBO J.*, 7:1197-1204). This mutant E2 gene was subcloned behind the cytomegalovirus promoter into an expression vector containing the neomycin resistance gene to generate plasmid pRC-tsE2. This plasmid was introduced into HeLa, SiHa, and C33A cells, and the number of G418-resistant colonies was determined after 21 days at 32 and 38° C. (Table 4). Following transfection at the nonpermissive temperature (38° C.), the cells were split and incubated at either 32 or 38° C. under G418 selection. At the permissive temperature (32° C.), tsE2 inhibited colony formation, similar to the effect of the wild-type E2-TA, in both the HeLa and SiHa cell lines. However, at the nonpermissive temperature (38° C.), there was no growth inhibition in any of the cell lines tested. In agreement with the results obtained with wild-type E2, no growth suppression was observed with tsE2 in C33A cells at the permissive temperature. Control transfections performed with the pRc-neo vector alone confirmed that the growth suppression observed in HeLa and SiHa cells was not due to temperature, since G418-resistant colonies appeared for both cell lines at 32°C.

TABLE 4

Temperature-sensitive growth phenotype of cells containing the E2 mutant[a]

| | No. of G418-resistant colonies | | | |
|---|---|---|---|---|
| | pRC-tsE2 | | pRC-neo | |
| Cell line | 32° C. | 38° C. | 32° C. | 38° C. |
| HeLa | 0 | 73 | 41 | 61 |
| SiHa | 0 | 86 | 37 | 77 |
| C33A | >500 | >500 | >500 | >500 |

[a]Indicated cell lines were transfected with 1 µg of pSV2neo and 10 µg of either BPV-1 tsE2 or vector alone.

pRC-tsE2 was used to generate a G418-resistant HeLa cell line at 38° C. which expressed the conditional E2 mutant protein (HeLa-tsE2). HeLa-tsE2 clonal lines were characterized for the ability to transactivate an E2-responsive plasmid and for their growth properties at 32 and 38° C. As a control, a G418-resistant HeLa cell line (HeLa-V) was also established by using the vector without insert. The HeLa-tsE2 cells were growth arrested at 32° C., whereas the HeLa-V cells were not. Fluorescence-activated cell sorting analysis indicated that the HeLa-tsE2 cells were arrested in G$_1$ when grown at 32° C., consistent with previously reported data indicating that BPV-1 E2 expression HeLa cells from a recombinant SV40 leads to a G$_1$ cell cycle arrest (Hwang et al. (1993) *J. Virol.*, 67:3720-3729). The HeLa-tsE2 cell line was characterized for HPV-18 RNA levels. At the permissive temperature, the level of E6/E7 message was at least three- to fourfold lower than in HeLa-tsE2 cells at 38° C. There was a temperature-dependent decrease of 1.5-fold in the HeLa-V cell line at 32° C. compared with HeLa-V cells grown at 38° C.

(vi) Effects of E2 Expression on Cellular Proteins in HeLa Cells.

The E2-dependent loss of E6/E7 message and growth arrest may be mediated through cellular targets of the E6 and E7 proteins. Since HPV-18 E6 promotes the degradation of p53, the decrease in expression of the endogenous viral mRNA would be predicted to result in lower levels of E6 and increased levels of p53. The levels of p53 were examined in the HeLa-tsE2 cell line following a shift to the permissive temperature. Immunoblot analysis of total cell extracts demonstrated a 20-fold increase in the level of p53 in HeLa-tsE2 cells shifted to 32° Compared with normal HeLa cells or HeLa-tsE2 cells grown at 38° C. A decrease in p53 levels was noted in HeLa-V cells at 32° C. The reason for this lowered level of p53 is not known, but this finding suggests that the destabilizing effect of E6 might be even greater than the 20-fold change in the HeLa-tsE2 cell line.

Induction of the cyclin-dependent kinase inhibitor p21/WAF1/Cip1/Sdi1 occurs in response to increased levels of p53 (Eldiery et al. (1993) *Cell,* 75:817-825). An increased level of p21 protein was observed in the HeLa-tsE2 cells after a shift to the permissive temperature (32° C.). Notably, in the HeLa-V cell line at 32° C., which had very low levels of p53, no p21 was detected.

To examine whether the increased levels of p21 in the HeLa-tsE2 cell line at the permissive temperature resulted in an inhibition of the cyclin-dependent kinases, cell lysates were prepared and immunoprecipitated with cyclin-specific antibodies, and kinase assays were performed with histone H1 as a substrate (Matsushime et al. (1994) *Mol. Cell Biol.,* 14:2066-2076). Cyclin E is associated with Cdk2 and is active in late $G_1$ (Dulic et al. (1993) *Proc. Natl. Acad. Sci. USA,* 90:11034-11038; Koff et al. 1992) *Science,* 257:1689-1694). Inhibition of the cyclin E-associated kinase activity was observed in the HeLa-tsE2 cells at the permissive temperature. The cyclin E-associated kinase was active in the HeLa-tsE2 cells at 38° C. and in the HeLa-V cells at both 32 and 38° C. Cyclin A-associated kinase activity was also inhibited in the HeLa-tsE2 cells at the permissive temperature but not at the nonpermissive temperature or in the HeLa-V cell line.

An immunoblot analysis of pRB was performed on extracts from the HeLa-tsE2 and HeLa-V cell lines grown at 32 or 38° C. Both the hyperphosphorylated and hypophosphorylated forms of pRB were detected in each case; however, the pRB forms in the HeLa-tsE2 cell line shifted to 32° C. were predominantly hypophosphorylated. There was little difference in the phosphorylation state of pRB in the HeLa-tsE2 cells grown at 38° C. and pRB in the HeLa-V control cell line at either temperature.

Figure 4:
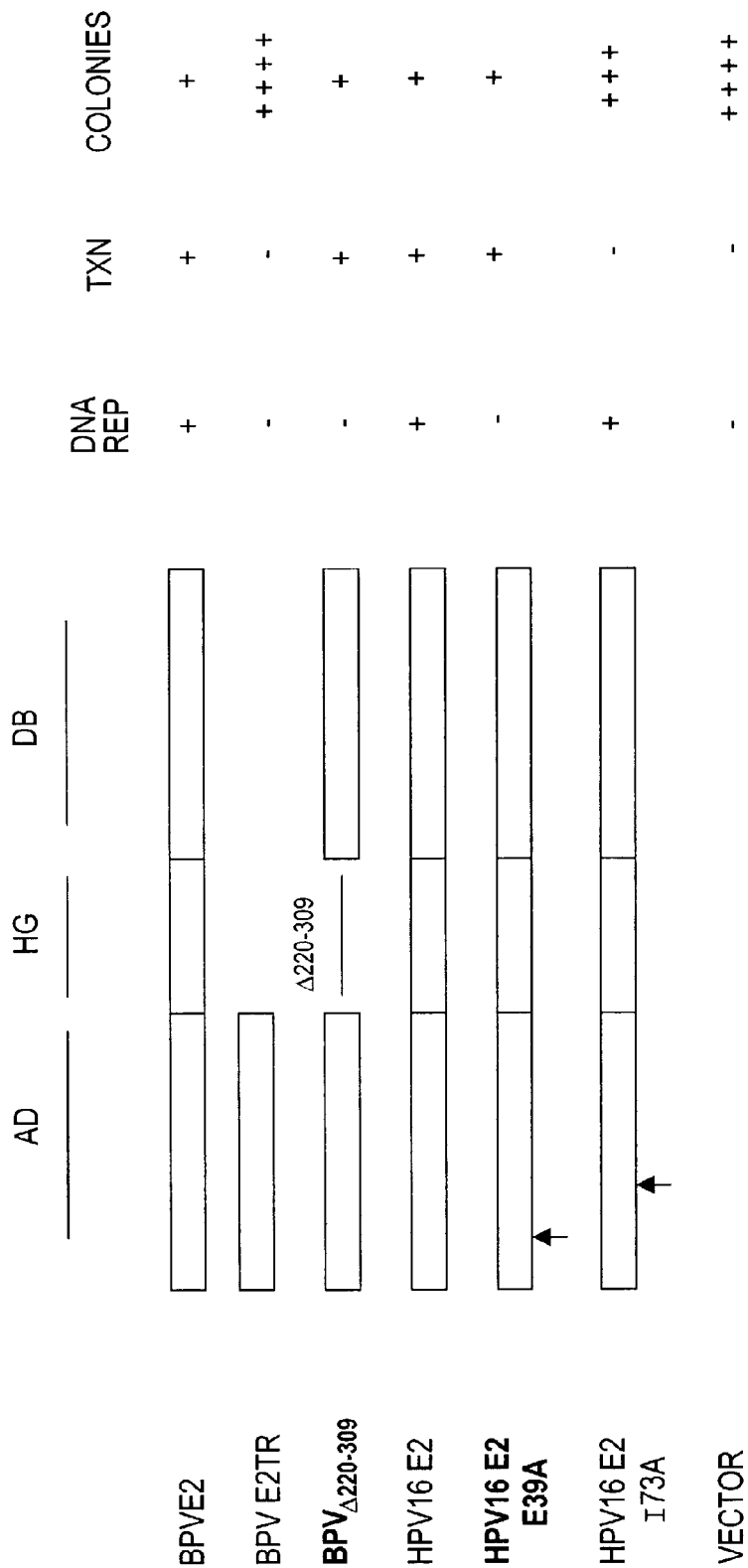
FIG. 4 shows a schematic of various HPV and BPV E2 polypeptides and the relative activity of these polypeptides in viral DNA replication (DNA REP), repression of viral transcription (TXN), and suppression of papillomavirus-mediated cell growth (COLONIES); AD, activation domain; HG, hinge region; DB, DNA-binding domain. Mutants marked in bold, i.e., BPV $E2_{\Delta 220\text{-}309}$ and $HPV_{(E39A)}$, show a desired therapeutic response in all three assays, i.e., no maintenance of viral replication, repression of viral gene expression, and suppression of viral-mediated cell proliferation.

(vii) Effects of E2 Expression (HPV16) on Growth Suppression, Transcription, and Virus Replication The above studies were extended with an E2 polypeptide from a high risk human strain of papillomavirus (HPV16). In this study, a structure-function analysis of the N-terminal domain of HPV 16 E2 protein was performed. Three different biological activities were examined for the HPV 16 E2 protein: transcriptional transactivation (which indicates the ability of the E2 polypeptide to repress viral transcription, see, e.g., Goodwin et al. (1998) *J. Virology* 72:3925-3934), enhancement of origin-dependent DNA replication, and repression of cell growth. By targeting highly conserved amino acids for alanine substitution mutagenesis, mutations were identified in the N-terminal domain that can disrupt either the transactivation or DNA replication functions of HPV16 E2 (see, e.g., E2 (E39A) and E2 (173A); Table 5 and FIG. 4). These observations indicate that these functions are distinct and separable. Furthermore, the binding capacity of E2 for E1 was observed to be critical for its function in origin-dependent DNA replication. Importantly, these studies allowed for the identification of an E2 mutant that can repress cell growth while avoiding the triggering of undesired viral replication (e.g., HPV E2 (E39A)).

TABLE 5

HPV E2 (E39A) represses cell growth but does not promote viral replication

| E2 Construct | DNA replication function | Transcriptional activation function | Number of Colonies | | |
|---|---|---|---|---|---|
| | | | Expt. 1 | Expt. 2 | Expt. 3 |
| Vector | − | − | 720 | 524 | 532 |
| BPV E2 | + | + | 19 | 40 | 5 |
| BPV E2TR | − | − | 632 | 336 | 642 |

TABLE 5-continued

HPV E2 (E39A) represses cell growth but does not promote viral replication

| E2 Construct | DNA replication function | Transcriptional activation function | Number of Colonies | | |
|---|---|---|---|---|---|
| | | | Expt. 1 | Expt. 2 | Expt. 3 |
| HPV 16E2 | + | + | 92 | 96 | 29 |
| HPV 16E2 E39A | − | + | 86 | 11 | 25 |
| HPV 16E2 173A | + | − | 170 | 404 | 119 |

In conclusion, this analysis of the HPV 16 E2 protein by alanine substitution mutagenesis of conserved amino acid residues in the N terminus has provided evidence that E2 is a multifunctional protein whose different activities can be separated. The strong transcriptional activation function of E2 can be dissociated from its ability to enhance E1-mediated, origin-specific DNA replication. The DNA replication function of E2 appears to depend on its ability to bind E1. Importantly, the above studies demonstrate that it is feasible to engineer E2 polypeptides defective for promoting viral replication and yet able to suppress cell growth and this is clearly exemplified by, e.g., this mutant, as well as the BPV mutant $E2_{\Delta 220\text{-}309}$ (see FIG. 4). The isolation of an E2 polypeptide defective for viral replication but able to suppress cell growth, e.g., in papillomavirus-infected cells has important therapeutic advantages. For example, such a polypeptide may be used to suppress growth in papillomavirus-infected cells without the danger of triggering virus replication in the cell.

Discussion

The E2 transactivation and DNA binding/dimerization domains were each necessary for E2-mediated growth suppression of HeLa cells. $E2_{>220\text{-}309}$, which is defective in the replication function but retains the ability to transactivate an E2-responsive plasmid (Winokur and McBride (1992) *EMBO J.,* 11:4111-4118), was able to suppress growth of HeLa cells, indicating that the growth-suppressive properties of E2 can be unlinked from its DNA replication properties. These same activities where also achieved using a altered E2 polypeptide from HPV16 by introducing a single amino acid substitution into the transactivation domain (i.e., E39A). Importantly, it was observed that the fusion of two other transactivation domains to the E2 DNA binding domain did not suppress the growth of HeLa cells, even though each of these chimeric proteins could function as E2-dependent transactivators in these cells. Therefore, some characteristic of the E2 transactivation domain is specific for cell growth suppression and is not shared with other transactivation domains. While not wishing to be bound by any particular theory, it is possible that the E2 transactivation domain recruits specific cellular factors to the promoter which may play a role in the transcriptional repression and growth suppression activities of E2.

The dependence of a functional transactivation domain may be in part due to its ability to relieve nucleosome-mediated repression. The E2 transactivation domain has been shown to counteract the nucleosome repression of DNA replication (Li et al. (1994) *PNAS,* 91:7051-7055). The transcriptional repression properties of the E2-TR have been characterized on transiently transfected naked DNA. This, however, cannot be the only explanation for E2-mediated growth suppression, since the VP16 transactivation domain also has the ability to relieve nucleosome repression, but in our experiments, expression of the chimeric protein does not result in growth suppression.

The growth-suppressive effect of E2 was demonstrated in other HPV-positive cell lines but not in HPV-negative cell lines by the cotransfection assay used in this study. These results demonstrate that E2 selectively represses cell growth in papillomavirus-infected cells and not in uninfected cells. Importantly, these observations indicate that the E2 polypeptides of the invention can be used therapeutically to selectivity arrest an undesired papillomavirus infections while leaving normal cellular growth unaffected. This result contrasts with the finding of Hwang et al. (Hwang et al. (1993) *J. Virol.*, 67:3720-3729), who observed a growth-suppressive effect with BPV-1 E2-TA in the HPV-negative cervical carcinoma cell line HT-3. One explanation for the difference between these two studies may involve the different assays used and different levels of expression of E2 achieved in the two experimental approaches. Our studies were done with DNA transfection, whereas the studies by Hwang et al. used the recombinant SV40 virus PAVA-E2, which resulted in much higher levels of protein expression. We have not been able to detect E2 protein by immunoblot analysis in HeLa cell lines transfected with the E2 plasmid, even though we can readily detect functional levels of E2 in transactivation of transcriptional repression assays. However, E2 is readily detectable by immunoblotting HeLa cells infected with the PAVA-E2 virus (Hwang et al. (1993) *J. Virol.*, 67:3720-3729), indicating a significantly higher level of expression. The two studies also differed in the experimental conditions to assess the biologic effects of E2 expression. Hwang et al. examined the transient effects of E2 by analyzing the cells 2 days postinfection. In the colony growth suppression assay used in our study, selection was maintained for 2 weeks, at which time the number of drug-resistant colonies was counted. Thus, the different effects of E2 observed on the growth of the HPV-negative HT-3 cell line may be due to differences in the assays, to the levels of E2 expression achieved by the different vectors, or to both. Nevertheless, it is the present findings which now provide the motivation to use E2 proteins to treat PV infected or transformed cells.

Repression of HPV-18 E6/E7 transcription was observed in the HeLa-tsE2 cells after a shift to the permissive temperature, resulting in a growth arrest. Our data indicate that in HeLa cells, the mechanism of E2-mediated growth arrest involves a decrease in E6 and E7 mRNA and reactivation of the p53/p21 and pRB pathways. The fact that the p21/Cdk inhibitory pathway is still intact and can be activated by disruption of E6 function suggests that therapeutic strategies targeted at interfering with E6 function could be effective in inhibition of cellular proliferation in HPV-positive cancers. We also observe an accumulation of hypophosphorylated pRB, which may be a consequence of a p53-mediated $G_1$ growth arrest (Slebos et al. (1994) *Proc. Natl. Acad. Sci. USA,* 91:5320-5324). Cells blocked in $G_1$ prior to activation of the cyclin D/Cdk complexes do not phosphorylate pRB. The shift in the phosphorylation state of RB to its hypophosphorylated form suggests that the cell cycle block occurs prior to the point of pRB phosphorylation. Our studies are in agreement with the observation that expression of antisense E6/E7 in C4-1, an HPV-18-derived cell line, was able to inhibit the growth rate of these cells (von Knebel-Doeberitz et al. (1988) *Cancer Res.,* 48 :3780-3785; von Knebel-Doeberitz et al. (1992) *Int. J. Cancer,* 51:831-834).

The studies presented here indicate that the transactivation domain of E2 is involved in the growth suppression and that the characteristic of the E2 transactivation domain in this suppression is not a general property shared with the VP16 and Sp1 transactivation domains.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

---

We claim:

1. An isolated polynucleotide encoding a functional portion of a human papillomavirus ad region and a functional portion of a human papillomavirus db region, wherein the encoded polypeptide comprises an altered hinge region modified by one or more amino acid substitutions, deletions, or additions as compared to wild type E2 polypeptide and selected for its ability to inhibit human papillomavirus DNA replication and the growth of cells infected with a papillomavirus when expressed in the cells, wherein the polynucleotide is present in a vector suitable for expression in the infected cells.

2. The isolated polynucleotide of claim 1, wherein the vector is a viral vector.

3. The isolated polynucleotide of claim 2, wherein the vector is an adenoviral vector.

4. A composition comprising the polynucleotide of any one of claims 1, 2 or 3 and a pharmaceutically acceptable carrier.

5. The polynucleotide of claim 1, wherein the human papillomavirus (HPV) sequence is selected from the group consisting of HPV-16, HPV-18, HPV-31, and HPV-33.

6. An isolated polynucleotide encoding an $E2_{ad/db}$ polypeptide, wherein the $E2_{ad/db}$ polypeptide comprises an altered hinge region modified by one or more amino acid substitutions, deletions, or additions as compared to wild type E2 polypeptide and selected for its ability to inhibit papillomavirus DNA replication and the growth of cells infected with a papillomavirus when expressed in the cells.

7. A composition comprising the polynucleotide of claim 6 and a pharmaceutically acceptable carrier.

8. The polynucleotide of claim 6, wherein the papillomavirus is selected from the group consisting of HPV-16, HPV-18, HPV-31, and HPV-33.

9. The isolated polynucleotide of claim 1, wherein the $E2_{ad/db}$ polypeptide comprises a deletion corresponding to amino acid residues 220-309 of BPV E2.

10. The isolated polynucleotide of claim 6, wherein the $E2_{ad/db}$ polypeptide comprises a deletion corresponding to amino acid residues 220-309 of BPV E2.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 1095 base pairs
      (B) TYPE: nucleic acid
      (C) STRANDEDNESS: both
      (D) TOPOLOGY: linear (ii) MOLECULE TYPE: DNA (genomic)

(ix) FEATURE:
      (A) NAME/KEY: CDS
      (B) LOCATION: 1..1095

(xi) SEQUENCE DESCRIPTION: SEQ ID NO: 1:

```
ATG GAG ACT CTT TGC CAA CGT TTA AAT GTG TGT CAG GAC AAA ATA CTA      48
Met Glu Thr Leu Cys Gln Arg Leu Asn Val Cys Gln Asp Lys Ile Leu
 1               5                  10                  15
```

```
ACA CAT TAT GAA AAT GAT AGT ACA GAC CTA CGT GAC CAT ATA GAC TAT        96
Thr His Tyr Glu Asn Asp Ser Thr Asp Leu Arg Asp His Ile Asp Tyr
             20                  25                  30

TGG AAA CAC ATG CGC CTA GAA TGT GCT ATT TAT TAC AAG GCC AGA GAA       144
Trp Lys His Met Arg Leu Glu Cys Ala Ile Tyr Tyr Lys Ala Arg Glu
         35                  40                  45

ATG GGA TTT AAA CAT ATT AAC CAC CAA GTG GTG CCA ACA CTG GCT GTA       192
Met Gly Phe Lys His Ile Asn His Gln Val Val Pro Thr Leu Ala Val
     50                  55                  60

TCA AAG AAT AAA GCA TTA CAA GCA ATT GAA CTG CAA CTA ACG TTA GAA       240
Ser Lys Asn Lys Ala Leu Gln Ala Ile Glu Leu Gln Leu Thr Leu Glu
 65                  70                  75                  80

ACA ATA TAT AAC TCA CAA TAT AGT AAT GAA AAG TGG ACA TTA CAA GAC       288
Thr Ile Tyr Asn Ser Gln Tyr Ser Asn Glu Lys Trp Thr Leu Gln Asp
                 85                  90                  95

GTT AGC CTT GAA GTG TAT TTA ACT GCA CCA ACA GGA TGT ATA AAA AAA       336
Val Ser Leu Glu Val Tyr Leu Thr Ala Pro Thr Gly Cys Ile Lys Lys
             100                 105                 110

CAT GGA TAT ACA GTG GAA GTG CAG TTT GAT GGA GAC ATA TGC AAT ACA       384
His Gly Tyr Thr Val Glu Val Gln Phe Asp Gly Asp Ile Cys Asn Thr
         115                 120                 125

ATG CAT TAT ACA AAC TGG ACA CAT ATA TAT ATT TGT GAA GAA GCA TCA       432
Met His Tyr Thr Asn Trp Thr His Ile Tyr Ile Cys Glu Glu Ala Ser
     130                 135                 140

GTA ACT GTG GTA GAG GGT CAA GTT GAC TAT TAT GGT TTA TAT TAT GTT       480
Val Thr Val Val Glu Gly Gln Val Asp Tyr Tyr Gly Leu Tyr Tyr Val
145                 150                 155                 160

CAT GAA GGA ATA CGA ACA TAT TTT GTG CAG TTT AAA GAT GAT GCA GAA       528
His Glu Gly Ile Arg Thr Tyr Phe Val Gln Phe Lys Asp Asp Ala Glu
                 165                 170                 175

AAA TAT AGT AAA AAT AAA GTA TGG GAA GTT CAT GCG GGT GGT CAG GTA       576
Lys Tyr Ser Lys Asn Lys Val Trp Glu Val His Ala Gly Gly Gln Val
             180                 185                 190

ATA TTA TGT CCT ACA TCT GTG TTT AGC AGC AAC GAA GTA TCC TCT CCT       624
Ile Leu Cys Pro Thr Ser Val Phe Ser Ser Asn Glu Val Ser Ser Pro
         195                 200                 205

GAA ATT ATT AGG CAG CAC TTG GCC AAC CAC CCC GCC GCG ACC CAT ACC       672
Glu Ile Ile Arg Gln His Leu Ala Asn His Pro Ala Ala Thr His Thr
     210                 215                 220

AAA GCC GTC GCC TTG GGC ACC GAA GAA ACA CAG ACG ACT ATC CAG CGA       720
Lys Ala Val Ala Leu Gly Thr Glu Glu Thr Gln Thr Thr Ile Gln Arg
225                 230                 235                 240

CCA AGA TCA GAG CCA GAC ACC GGA AAC CCC TGC CAC ACC ACT AAG TTG       768
Pro Arg Ser Glu Pro Asp Thr Gly Asn Pro Cys His Thr Thr Lys Leu
                 245                 250                 255

TTG CAC AGA GAC TCA GTG GAC AGT GCT CCA ATC CTC ACT GCA TTT AAC       816
Leu His Arg Asp Ser Val Asp Ser Ala Pro Ile Leu Thr Ala Phe Asn
             260                 265                 270

AGC TCA CAC AAA GGA CGG ATT AAC TGT AAT AGT AAC ACT ACA CCC ATA       864
Ser Ser His Lys Gly Arg Ile Asn Cys Asn Ser Asn Thr Thr Pro Ile
         275                 280                 285

GTA CAT TTA AAA GGT GAT GCT AAT ACT TTA AAA TGT TTA AGA TAT AGA       912
Val His Leu Lys Gly Asp Ala Asn Thr Leu Lys Cys Leu Arg Tyr Arg
     290                 295                 300

TTT AAA AAG CAT TGT ACA TTG TAT ACT GCA GTG TCG TCT ACA TGG CAT       960
Phe Lys Lys His Cys Thr Leu Tyr Thr Ala Val Ser Ser Thr Trp His
305                 310                 315                 320

TGG ACA GGA CAT AAT GTA AAA CAT AAA AGT GCA ATT GTT ACA CTT ACA      1008
Trp Thr Gly His Asn Val Lys His Lys Ser Ala Ile Val Thr Leu Thr
```

-continued

```
                325                 330                 335
TAT GAT AGT GAA TGG CAA CGT GAC CAA TTT TTG TCT CAA GTT AAA ATA    1056
Tyr Asp Ser Glu Trp Gln Arg Asp Gln Phe Leu Ser Gln Val Lys Ile
                340                 345                 350

CCA AAA ACT ATT ACA GTG TCT ACT GGA TTT ATG TCT ATA                1095
Pro Lys Thr Ile Thr Val Ser Thr Gly Phe Met Ser Ile
                355                 360                 365

(2) INFORMATION FOR SEQ ID NO: 2:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Thr Leu Cys Gln Arg Leu Asn Val Cys Gln Asp Lys Ile Leu
 1               5                  10                  15

Thr His Tyr Glu Asn Asp Ser Thr Asp Leu Arg Asp His Ile Asp Tyr
                20                  25                  30

Trp Lys His Met Arg Leu Glu Cys Ala Ile Tyr Tyr Lys Ala Arg Glu
            35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
                100                 105                 110

His Gly Tyr Thr Val Glu Val Gln Phe Asp Gly Asp Ile Cys Asn Thr
            115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
                180                 185                 190

Ile Leu Cys Pro Thr Ser Val Phe Ser Ser Asn Glu Val Ser Ser Pro
            195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
                260                 265                 270

Ser Ser His Lys Gly Arg Ile Asn Cys Asn Ser Asn Thr Thr Pro Ile
            275                 280                 285

Val His Leu Lys Gly Asp Ala Asn Thr Leu Lys Cys Leu Arg Tyr Arg
    290                 295                 300
```

```
            Phe Lys Lys His Cys Thr Leu Tyr Thr Ala Val Ser Ser Thr Trp His
            305                 310                 315                 320

Trp Thr Gly His Asn Val Lys His Lys Ser Ala Ile Val Thr Leu Thr
                            325                 330                 335

Tyr Asp Ser Glu Trp Gln Arg Asp Gln Phe Leu Ser Gln Val Lys Ile
                        340                 345                 350

Pro Lys Thr Ile Thr Val Ser Thr Gly Phe Met Ser Ile
                    355                 360                 365

(2) INFORMATION FOR SEQ ID NO: 3:

(i) SEQUENCE CHARACTERISTICS:
        (A) LENGTH: 1095 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: CDS
        (B) LOCATION: 1..1095

(xi) SEQUENCE DESCRIPTION: SEQ ID NO: 3:

ATG CAG ACA CCG AAG GAA ACC CTT TCG GAA CGT TTA AGT TGC GTG CAG              48
Met Gln Thr Pro Lys Glu Thr Leu Ser Glu Arg Leu Ser Cys Val Gln
  1               5                  10                  15

GAC AAA ATC ATA GAC CAC TAT GAA AAT GAC AGT AAA GAC ATA GAC AGC              96
Asp Lys Ile Ile Asp His Tyr Glu Asn Asp Ser Lys Asp Ile Asp Ser
             20                  25                  30

CAA ATA CAG TAT TGG CAA CTA ATA CGT TGG GAA AAT GCA ATA TTC TTT             144
Gln Ile Gln Tyr Trp Gln Leu Ile Arg Trp Glu Asn Ala Ile Phe Phe
         35                  40                  45

GCA GCA AGG GAA CAT GGC ATA CAG ACA TTA AAC CAC CAG GTG GTG CCA             192
Ala Ala Arg Glu His Gly Ile Gln Thr Leu Asn His Gln Val Val Pro
     50                  55                  60

GCC TAT AAC ATT TCA AAA AGT AAA GCA CAT AAA GCT ATT GAA CTG CAA             240
Ala Tyr Asn Ile Ser Lys Ser Lys Ala His Lys Ala Ile Glu Leu Gln
 65                  70                  75                  80

ATG GCC CTA CAA GGC CTT GCA CAA AGT CGA TAC AAA ACC GAG GAT TGG             288
Met Ala Leu Gln Gly Leu Ala Gln Ser Arg Tyr Lys Thr Glu Asp Trp
                 85                  90                  95

ACA CTG CAA GAC ACA TGC GAG GAA CTA TGG AAT ACA GAA CCT ACT CAC             336
Thr Leu Gln Asp Thr Cys Glu Glu Leu Trp Asn Thr Glu Pro Thr His
            100                 105                 110

TGC TTT AAA AAA GGT GGC CAA ACA GTA CAA GTA TAT TTT GAT GGC AAC             384
Cys Phe Lys Lys Gly Gly Gln Thr Val Gln Val Tyr Phe Asp Gly Asn
        115                 120                 125

AAA GAC AAT TGT ATG ACC TAT GTA GCA TGG GAC AGT GTG TAT TAT ATG             432
Lys Asp Asn Cys Met Thr Tyr Val Ala Trp Asp Ser Val Tyr Tyr Met
    130                 135                 140

ACT GAT GCA GGA ACA TGG GAC AAA ACC GCT ACC TGT GTA AGT CAC AGG             480
Thr Asp Ala Gly Thr Trp Asp Lys Thr Ala Thr Cys Val Ser His Arg
145                 150                 155                 160

GGA TTG TAT TAT GTA AAG GAA GGG TAC AAC ACG TTT TAT ATA GAA TTT             528
Gly Leu Tyr Tyr Val Lys Glu Gly Tyr Asn Thr Phe Tyr Ile Glu Phe
                165                 170                 175

AAA AGT GAA TGT GAA AAA TAT GGG AAC ACA GGT ACG TGG GAA GTA CAT             576
Lys Ser Glu Cys Glu Lys Tyr Gly Asn Thr Gly Thr Trp Glu Val His
            180                 185                 190

TTT GGG AAT AAT GTA ATT GAT TGT AAT GAC TCT ATG TGC AGT ACC AGT             624
Phe Gly Asn Asn Val Ile Asp Cys Asn Asp Ser Met Cys Ser Thr Ser
```

-continued

```
                      195                 200                 205
GAC GAC ACG GTA TCC GCT ACT CAG CTT GTT AAA CAG CTA CAG CAC ACC      672
Asp Asp Thr Val Ser Ala Thr Gln Leu Val Lys Gln Leu Gln His Thr
        210                 215                 220

CCC TCA CCG TAT TCC AGC ACC GTG TCC GTG GGC ACC GCA AAG ACC TAC      720
Pro Ser Pro Tyr Ser Ser Thr Val Ser Val Gly Thr Ala Lys Thr Tyr
225                 230                 235                 240

GGC CAG ACG TCG GCT GCT ACA CGA CCT GGA CAC TGT GGA CTC GCG GAG      768
Gly Gln Thr Ser Ala Ala Thr Arg Pro Gly His Cys Gly Leu Ala Glu
                245                 250                 255

AAG CAG CAT TGT GGA CCT GTC AAC CCA CTT CTC GGT GCA GCT ACA CCT      816
Lys Gln His Cys Gly Pro Val Asn Pro Leu Leu Gly Ala Ala Thr Pro
        260                 265                 270

ACA GGC AAC AAC AAA AGA CGG AAA CTC TGT AGT GGT AAC ACT ACG CCT      864
Thr Gly Asn Asn Lys Arg Arg Lys Leu Cys Ser Gly Asn Thr Thr Pro
                275                 280                 285

ATA ATA CAT TTA AAA GGT GAC AGA AAC AGT TTA AAA TGT TTA CGG TAC      912
Ile Ile His Leu Lys Gly Asp Arg Asn Ser Leu Lys Cys Leu Arg Tyr
        290                 295                 300

AGA TTG CGA AAA CAT AGC GAC CAC TAT AGA GAT ATA TCA TCC ACC TGG      960
Arg Leu Arg Lys His Ser Asp His Tyr Arg Asp Ile Ser Ser Thr Trp
305                 310                 315                 320

CAT TGG ACA GGT GCA GGC AAT GAA AAA ACA GGA ATA CTG ACT GTA ACA     1008
His Trp Thr Gly Ala Gly Asn Glu Lys Thr Gly Ile Leu Thr Val Thr
                325                 330                 335

TAC CAT AGT GAA ACA CAA AGA ACA AAA TTT TTA AAT ACT GTT GCA ATT     1056
Tyr His Ser Glu Thr Gln Arg Thr Lys Phe Leu Asn Thr Val Ala Ile
        340                 345                 350

CCA GAT AGT GTA CAA ATA TTG GTG GGA TAC ATG ACA ATG                 1095
Pro Asp Ser Val Gln Ile Leu Val Gly Tyr Met Thr Met
        355                 360                 365
```

(2) INFORMATION FOR SEQ ID NO: 4:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gln Thr Pro Lys Glu Thr Leu Ser Glu Arg Leu Ser Cys Val Gln
1               5                   10                  15

Asp Lys Ile Ile Asp His Tyr Glu Asn Asp Ser Lys Asp Ile Asp Ser
            20                  25                  30

Gln Ile Gln Tyr Trp Gln Leu Ile Arg Trp Glu Asn Ala Ile Phe Phe
        35                  40                  45

Ala Ala Arg Glu His Gly Ile Gln Thr Leu Asn His Gln Val Val Pro
    50                  55                  60

Ala Tyr Asn Ile Ser Lys Ser Lys Ala His Lys Ala Ile Glu Leu Gln
65                  70                  75                  80

Met Ala Leu Gln Gly Leu Ala Gln Ser Arg Tyr Lys Thr Glu Asp Trp
            85                  90                  95

Thr Leu Gln Asp Thr Cys Glu Glu Leu Trp Asn Thr Glu Pro Thr His
            100                 105                 110

Cys Phe Lys Lys Gly Gly Gln Thr Val Gln Val Tyr Phe Asp Gly Asn
        115                 120                 125

Lys Asp Asn Cys Met Thr Tyr Val Ala Trp Asp Ser Val Tyr Tyr Met
```

-continued

```
            130                 135                 140
Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
                180                 185                 190

Phe Gly Asn Asn Val Ile Asp Cys Asn Asp Ser Met Cys Ser Thr Ser
                195                 200                 205

Asp Asp Thr Val Ser Ala Thr Gln Leu Val Lys Gln Leu Gln His Thr
210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
                260                 265                 270

Thr Gly Asn Asn Lys Arg Arg Lys Leu Cys Ser Gly Asn Thr Thr Pro
                275                 280                 285

Ile Ile His Leu Lys Gly Asp Arg Asn Ser Leu Lys Cys Leu Arg Tyr
                290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
                325                 330                 335

Tyr His Ser Glu Thr Gln Arg Thr Lys Phe Leu Asn Thr Val Ala Ile
                340                 345                 350

Pro Asp Ser Val Gln Ile Leu Val Gly Tyr Met Thr Met
                355                 360                 365

(2) INFORMATION FOR SEQ ID NO: 5:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO: 5:

Met Glu Thr Leu Cys Gln Arg Leu Asn Val Cys Gln Asp Lys Ile Leu
 1               5                  10                  15

Thr His Tyr Glu Asn Asp Ser Thr Asp Leu Arg Asp His Ile Asp Tyr
                20                  25                  30

Trp Lys His Met Arg Leu Ala Cys Ala Ile Tyr Tyr Lys Ala Arg Glu
            35                  40                  45

Met Gly Phe Lys His Ile Asn His Gln Val Val Pro Thr Leu Ala Val
            50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
            115                 120                 125
```

-continued

```
Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
        355                 360                 365
```